(12) United States Patent
Guerin et al.

(10) Patent No.: US 8,183,245 B2
(45) Date of Patent: May 22, 2012

(54) PYRAZINE SUBSTITUTED PYRROLOPYRIDINES AS INHIBITORS OF JAK AND PDK1

(75) Inventors: David J. Guerin, Natick, MA (US); Joos Jung, Newton, MA (US); Elizabeth Stanton, Medfield, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 115 days.

(21) Appl. No.: 12/682,612

(22) PCT Filed: Oct. 21, 2008

(86) PCT No.: PCT/US2008/011971
§ 371 (c)(1),
(2), (4) Date: Apr. 12, 2010

(87) PCT Pub. No.: WO2009/054941
PCT Pub. Date: Apr. 30, 2009

(65) Prior Publication Data
US 2010/0210623 A1 Aug. 19, 2010

Related U.S. Application Data

(60) Provisional application No. 61/000,343, filed on Oct. 25, 2007.

(51) Int. Cl.
*A61K 31/4965* (2006.01)

(52) U.S. Cl. .............. 514/255.05; 544/359; 544/405; 546/113; 546/200; 548/373.1; 548/518; 548/950; 549/356

(58) Field of Classification Search .......... 514/255.05; 544/359, 405; 546/113, 200; 548/373.1, 548/518, 950; 549/356
See application file for complete search history.

(56) References Cited

U.S. PATENT DOCUMENTS
2007/0043068 A1 2/2007 Arnold et al.

FOREIGN PATENT DOCUMENTS
| WO | WO2005/095400 | 10/2005 |
| WO | WO2006/063167 | 6/2006 |
| WO | WO2006/124862 | 11/2006 |
| WO | WO2007/002433 | 1/2007 |
| WO | WO 2009/054941 | * 4/2009 |

OTHER PUBLICATIONS
Jordan, V. C. Nature Reviews: Drug Discovery, 2, 2003, 205.*
Hackam, et al. JAMA, 296(14), 2006, 1731-1732.*

* cited by examiner

*Primary Examiner* — James O Wilson
*Assistant Examiner* — Douglas M Willis
(74) *Attorney, Agent, or Firm* — Peter Haeberli; David A. Muthard

(57) ABSTRACT

The present invention relates to pyrazine substituted pyrrolopyridines having formula (I)

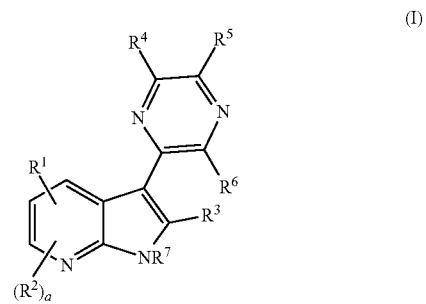

useful as inhibitors of JAK kinases (JAK1, JAK2, JAK3 and/or TYK2) and/or PDK1 and for the treatment of myeloproliferative disorders or other cancers.

8 Claims, No Drawings

PYRAZINE SUBSTITUTED PYRROLOPYRIDINES AS INHIBITORS OF JAK AND PDK1

This application is a §371 application of PCT/US2008/011971 that was filed on Oct. 21, 2008, which claims priority from the U.S. Provisional Application No. 61/000,343, filed on Oct. 25, 2007, now expired.

BACKGROUND OF THE INVENTION

The present invention relates to pyrazine substituted pyrrolopyridines which are inhibitors of JAK kinases (JAK1, JAK2, JAK3 and/or TYK2) and/or PDK1 and are thus useful for the treatment of myeloproliferative disorders or cancer.

Janus kinase (JAK) is a family of intracellular non-receptor tyrosine kinases, ranging from 120-140 kDa, that transduce cytokine-mediated signals via the JAK-STAT pathway. The JAK family plays a role in the cytokine-dependent regulation of proliferation and function of cells involved in immune response. Currently, there are four known mammalian JAK family members: JAK1, JAK2, JAK3 and TYK2.

JAK1, JAK2 and TYK2 are ubiquitously expressed whereas JAK3 is expressed in the myeloid and lymphoid lineages. The JAK family members are non-receptor tyrosine kinases that associate with many hematopoietin cytokines, receptor tyrosine kinases and GPCR's. JAK1−/− mice were found to be developmentally similar to the JAK1+/+ although they weighed 40% less than the wild-type and failed to nurse at birth. These pups were not viable and died within 24 hours of birth (Meraz et al Cell, 1998, 373-383). JAK1 deficiency led to reduced number of thymocytes, pre-B cells and mature T and B lymphocytes. TYK2(−/−) mice, on the other hand, are viable, demonstrating subtle defects in their response to IFN-α/β and IL-10 and profound defects to the response of IL-12 and LPS.

The breast cancer susceptibility protein (BRCA1) acts as a tumor suppressor and contributes to cell proliferation, cycle regulation, as well as DNA damage and repair. BRCA1 (−/−) mice develop normally but die by 7.5 days post embryo suggesting a key role of BRCA1 for development. Mice in which the BRCA1 protein was overexpressed led to inhibition of cell growth and sensitized cells to cytotoxic reagents. In the human prostate cancer cell line Du-145 (Gao FEBS Letters 2001, 488, 179-184), enhanced expression of BRCA1 was found to correlate with constitutive activation of STAT3 as well as activation of JAK1 and JAK2. Moreover, antisense oligonucleotides selective for STAT3 led to significant inhibition of cell proliferation and apoptosis in Du-145 cells. This data supports the potential utility of JAK1 and JAK2 inhibitors in the treatment of prostate cancer.

Campbell et al (Journal of Biological Chemistry 1997, 272, 2591-2594) has reported that STAT3 is constitutively activated in v-Src transformed cells. To test whether STAT3 activation resulted via signaling through the JAK-STAT pathway, three fibroblast cell lines (NIH3T3, Balb/c, and 3Y1) were transformed with v-Src. The level of JAK1 phosphorylation in NIH3T3 cells was markedly increased in cells overexpressed with v-Src or mutant c-Src (Y527F) compared to those in the less transforming c-Src. This result correlated with increased JAK1 enzymatic activity. Similar results were observed with JAK2 albeit to a lesser extent. These results are consistent with constitutive activation of JAK1 and possibly JAK2 which contribute to the hyperactivation of STAT3 in Src-transformed cells.

Asthma is a disease that is increasing in prevalence and results in "airway obstruction, airway hyperresponsiveness, and airway inflammation and remodeling" (Pernis, The Journal of Clinical Investigation 2002, 109, 1279-1283). A common cause is the inappropriate immune responses to environmental antigens usually involving CD4+ T helper cells (TH2) which are triggered from cytokines IL-4, IL-5, IL-6, IL-10, and IL-13 which signal through JAK1/JAK3-STAT6 pathway. TH1 cells are thought to be involved with the "delayed-type hypersensitivity responses" which secrete IL-2, IFN-γ, and TNF-β and signal through the JAK2/TYK2-STAT4 pathway. STAT6 (−/−) mice were protected from AHR when challenged with environmental antigens and showed no increase in IgE levels or the quantity of mucous containing cells.

JAK2 is a cytoplasmic protein-tyrosine kinase that catalyzes the transfer of the gamma-phosphate group of adenosine triphosphate to the hydroxyl groups of specific tyrosine residues in signal transduction molecules. JAK2 mediates signaling downstream of cytokine receptors after ligand-induced autophosphorylation of both receptor and enzyme. The main downstream effectors of JAK2 are a family of transcription factors known as signal transducers and activators of transcription (STAT) proteins. Studies have disclosed an association between an activating JAK2 mutation (JAK2V617F) and myeloproliferative disorders. The myeloproliferative disorders, a subgroup of myeloid malignancies, are clonal stem cell diseases characterized by an expansion of morphologically mature granulocyte, erythroid, megakaryocyte, or monocyte lineage cells. Myeloproliferative disorders (MPD) include polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES), juvenile myelomonocytic leukemia (JMML) and systemic mast cell disease (SMCD). It has been suggested that abnormalties in signal transduction mechanisms, including constitutive activation of protein tyrosine kinases, initiate MPD.

JAK3 associates with the common gamma chain of the extracellular receptors for the following interleukins: IL-2, IL-4, IL-7, IL-9 and IL-15. A JAK3 deficiency is associated with an immune compromised (SCID) phenotype in both rodents and humans. The SCID phenotype of JAK3−/− mammals and the lymphoid cell specific expression of JAK3 are two favorable attributes of a target for an immune suppressant. Data suggests that inhibitors of JAK3 could impede T-cell activation and prevent rejection of grafts following transplant surgery, or to provide therapeutic benefit to patients suffering autoimmune disorders. PDK1 is a Ser/Thr protein kinase possessing a kinase domain at its N-terminus (residues 70-359) and a Pleckstrin homology (PH) domain at its C-terminus (residues 459-550). The kinase can phosphorylate and activate a number of kinases in the AGC kinase superfamily, including Akt/protein kinase B, protein kinase C (PKC), PKC-related kinases (PRK1 and PRK2), p70 ribosomal S6-kinase (S6K1) and serum and glucocorticoid-regulated kinase (SGK). Akt comprises a family of Ser/Thr protein kinases containing three highly homologous members (AKT1, AKT2 and AKT3) and its activation in cells by PDK1 requires stimulation of phosphoinositide 3-kinase (PI 3-kinase) (Feldman, Richard I., et al., *The Journal of Biological Chemistry*, Vol. 280, No. 20, Issue of May 20, pp. 19867-19874, 2005). The activation of Akt in tumor cells has been shown to have multiple upstream effects that promote disease progression, including suppression of apoptosis and stimulation of tumor cell proliferation, metabolism and angiogenesis. Thus the PI 3-kinase/PDK1/Akt signaling pathway plays a key role in regulating cancer cell growth, invasion, apoptosis and tumor angiogenesis. Furthermore, this pathway has been found to be highly activated in common cancers, including melanoma and haematological, breast, colon, pancreatic, prostate and ovarian cancers (Feldman, Richard I., et al, supra). The PI 3-kinase/PDK1/Akt signaling pathway is therefore a useful target for the developments of anticancer agents.

Structurally related JAK inhibitors have previously been described in WO2005/095400 and WO2007/002433.

The instant invention provides compounds which inhibit the activity of JAK kinases (JAK1, JAK2, JAK3 and/or TYK2) and/or PDK1. The present invention provides compounds of formula I:

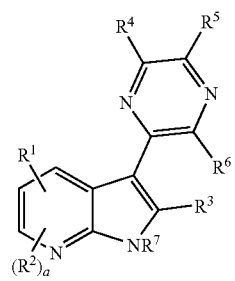

(I)

wherein:

a is 0, 1 or 2;

each of $R^1$ and $R^2$ is independently hydroxy, cyano, halogen, $C_{1-6}$alkyl, $C_{2-10}$alkenyl, halo$C_{1-6}$alkyl, hydroxy$C_{1-6}$alkyl, $C_{1-6}$alkylcarbonyl, $C_{1-6}$alkoxy, halo$C_{1-6}$alkoxy, $C_{1-6}$alkoxycarbonyl, carboxy, nitro, $NR^xR^y$, $CONR^xR^y$, $NR^x(CONR^xR^y)$, $S(O)_rNR^xR^y$ or a ring which is: $C_{6-10}$aryl, $C_{6-10}$aryloxy, $C_{6-10}$aryl$C_{1-6}$alkyl, $C_{6-10}$arylcarbonyl, $C_{3-10}$cycloalkyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O, and S, not more than one heteroatom of which is O or S, a 6 membered heteroaromatic ring containing 1, 2 or 3 N atoms or a 7-15 membered unsaturated, partially saturated or saturated heterocyclic ring containing 1, 2, 3 or 4 heteroatoms independently selected from N, O and S; any of which rings being optionally substituted by one or more groups independently selected from $R^a$;

$R^3$ is hydrogen or $C_{1-6}$alkyl;

$R^4$ is hydrogen, -L-$R^b$ or -M-$R^c$;

each of $R^5$, $R^6$ and $R^7$ is independently selected from hydrogen, hydroxy, cyano, halogen, $C_{1-6}$alkyl, $C_{2-10}$alkenyl, halo$C_{1-6}$alkyl, hydroxy$C_{1-6}$alkyl, $C_{1-6}$alkylcarbonyl, $C_{1-6}$alkoxy, halo$C_{1-6}$alkoxy, $C_{1-6}$alkoxycarbonyl, carboxy, nitro, $NR^xR^y$ or a ring which is: $C_{6-10}$aryl, $C_{6-10}$aryl$C_{1-6}$alkyl, $C_{3-10}$cycloalkyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 nitrogen atoms or a 7-15 membered unsaturated, partially saturated or saturated heterocyclic ring containing 1, 2, 3 or 4 heteroatoms independently selected from N, O and S; any of which rings being optionally substituted by one or more groups independently selected from hydroxy, cyano, halogen, $C_{1-6}$alkyl, $C_{1-6}$alkoxy, $C_{2-10}$alkenyl, halo$C_{1-6}$alkyl, amino, $C_{1-6}$alkylamino and di($C_{1-6}$alkyl)amino;

each of L and M is a direct bond, —O($CR^vR^w$)$_b$[N($R^z$)]$_c$— or —N($R^z$)($CR^vR^w$)$_b$—;

b is 0, 1, 2, 3 or 4;

c is 0 or 1;

r is 0, 1 or 2;

each $R^a$ is independently selected from hydroxy, oxo, cyano, halogen, $C_{1-6}$alkyl, $C_{2-10}$alkenyl, halo$C_{1-6}$alkyl, $C_{1-6}$alkylcarbonyl, $C_{1-6}$alkoxy, halo$C_{1-6}$alkoxy, hydroxy$C_{1-6}$alkyl, $C_{1-6}$alkoxycarbonyl, carboxy, $NR^xR^y$ or a ring which is: $C_{6-10}$aryl, $C_{6-10}$aryl$C_{1-6}$alkyl, $C_{3-10}$cycloalkyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 nitrogen atoms or a 7-15 membered unsaturated, partially saturated or saturated heterocyclic ring containing 1, 2, 3 or 4 heteroatoms independently selected from N, O and S; any of which rings being optionally substituted by one or more groups independently selected from hydroxy, cyano, halogen, $C_{1-6}$alkyl, $C_{1-6}$alkoxy, $C_{2-10}$alkenyl, halo$C_{1-6}$alkyl, amino, $C_{1-6}$alkylamino and di($C_{1-6}$alkyl)amino;

$R^b$ is hydroxy, cyano, halogen, $C_{1-6}$alkyl, $C_{2-10}$alkenyl, halo$C_{1-6}$alkyl, hydroxy$C_{1-6}$alkyl, $C_{1-6}$alkylcarbonyl, $C_{1-6}$alkoxy, halo$C_{1-6}$alkoxy, $C_{1-6}$alkoxycarbonyl, carboxy, nitro or $NR^xR^y$;

$R^c$ is $C_{3-10}$cycloalkyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O, and S, not more than one heteroatom of which is O or S, a 6 membered heteroaromatic ring containing 1, 2 or 3 N atoms or a 7-15 membered unsaturated, partially saturated or saturated heterocyclic ring containing 1, 2, 3 or 4 heteroatoms independently selected from N, O and S; optionally substituted by one or more groups independently selected from $R^d$;

each $R^d$ is independently selected from hydroxy, oxo, cyano, halogen, $C_{1-6}$alkyl, $C_{2-10}$alkenyl, halo$C_{1-6}$alkyl, $C_{1-6}$alkylcarbonyl, $C_{1-6}$alkoxy, halo$C_{1-6}$alkoxy, hydroxy$C_{1-6}$alkyl, $C_{1-6}$alkoxycarbonyl, carboxy, $NR^xR^y$ or a ring which is: $C_{6-10}$aryl, $C_{6-10}$aryl$C_{1-6}$alkyl, $C_{3-10}$cycloalkyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 nitrogen atoms or a 7-15 membered unsaturated, partially saturated or saturated heterocyclic ring containing 1, 2, 3 or 4 heteroatoms independently selected from N, O and S; any of which rings being optionally substituted by one or more groups independently selected from hydroxy, cyano, halogen, $C_{1-6}$alkyl, $C_{1-6}$alkoxy, $C_{2-10}$alkenyl, halo$C_{1-6}$alkyl, amino, $C_{1-6}$alkylamino and di($C_{1-6}$alkyl)amino;

each of $R^v$ and $R^w$ is independently hydrogen, $C_{1-6}$alkyl, halogen, hydroxy or halo$C_{1-6}$alkyl;

each of $R^x$ and $R^y$ is independently hydrogen, $C_{1-6}$alkyl, $C_{1-6}$alkylcarbonyl, halo$C_{1-6}$alkyl or hydroxy$C_{1-6}$alkyl;

$R^z$ is hydrogen or $C_{1-6}$alkyl;

or a pharmaceutically acceptable salt, stereoisomer or tautomer thereof.

In an embodiment a is 0.

In an embodiment when $R^1$ is a ring it is optionally substituted by one, two or three independently selected $R^a$ groups. In another embodiment the $R^1$ ring is unsubstituted or monosubstituted.

In an embodiment $R^1$ is azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O, and S, not more than one heteroatom of which is O or S, a 6 membered heteroaromatic ring containing 1, 2 or 3 N atoms or a 7-15 membered unsaturated, partially saturated or saturated heterocyclic ring containing 1, 2, 3 or 4 heteroatoms independently selected from N, O and S; optionally substituted by one or more groups independently selected from $R^a$.

In another embodiment $R^1$ is a 5 membered heteroaromatic ring containing 1, 2, 3 or 4 heteroatoms independently selected from N, O and S, not more than one heteroatom of which is O or S; optionally substituted by one, two or three groups independently selected from $R^a$.

In another embodiment $R^1$ is pyrazolyl optionally substituted by one, two or three groups independently selected from $R^a$.

In an embodiment when $R^a$ is a ring it is optionally substituted by one, two or three independently selected groups.

In an embodiment $R^a$ is $C_{1-6}$alkyl, halo$C_{1-6}$alkyl or hydroxy$C_{1-6}$alkyl.

Particular $R^a$ groups include methyl, ethyl, cyclopropylmethyl, hydroxyethyl and trifluoroethyl.

Specific $R^a$ groups include methyl, ethyl, cyclopropylmethyl, 2-hydroxyethyl and 2,2,2-trifluoroethyl.

Particular $R^1$ groups are methylpyrazolyl, pyrazolyl, ethylpyrazolyl, (cyclopropylmethyl)pyrazolyl, (hydroxyethyl)pyrazolyl and (trifluoroethyl)pyrazolyl.

Specific $R^1$ groups are 1-methyl-1H-pyrazol-4-yl, 1H-pyrazol-4-yl, 1-ethyl-1H-pyrazol-4-yl, 1-(cyclopropylmethyl)-1H-pyrazol-4-yl, 1-(2-hydroxyethyl)-1H-pyrazol-4-yl and 1-(2,2,2-trifluoroethyl)-1H-pyrazol-4-yl.

In an embodiment when $R^2$ is a ring it is optionally substituted by one, two or three independently selected $R^a$ groups.

In an embodiment $R^3$ is hydrogen.

In an embodiment $R^4$ is -L-$R^b$ or -M-$R^c$.

In one embodiment $R^4$ is -L-$R^b$. In another embodiment $R^4$ is -M-$R^c$.

In an embodiment L is —O(CR$^v$R$^w$)$_b$— or —N(R$^z$)(CR$^v$R$^w$)$_b$—.

Particular L groups are —O(CH$_2$)(CHCH$_3$)—, —O(CHCH$_3$)(CH)—, —NH(CH$_2$)$_2$—, —NH(CH$_2$)$_3$— and —O(CH$_2$)(CHCF$_3$)—.

In an embodiment M is a direct bond, —O—, —N(R$^z$)— or —O(CR$^v$R$^w$)$_b$N(R$^z$)—.

Particular M groups are a direct bond, —O—, —NH—, —N(CH$_3$)—, —N(CH$_2$CH$_3$)—, —N[(CH$_2$)(CH$_3$)]— or —O(CH$_2$)$_2$NH—.

In an embodiment M is —O—.

In an embodiment b is 0, 1 or 2.

In an embodiment c is 0. In another embodiment c is 1.

In an embodiment $R^b$ is hydroxy or NR$^x$R$^y$.

Specific $R^b$ groups are hydroxy and amino.

In an embodiment $R^c$ is optionally substituted by one, two or three independently selected $R^d$ groups. In another embodiment $R^c$ is unsubstituted or monosubstituted.

In an embodiment $R^c$ is azetidinyl or a 5, 6 or 7 membered saturated or partially saturated heterocyclic ring containing 1, 2 or 3 atoms independently selected from N, O and S, optionally substituted by one, two or three independently selected $R^d$ groups.

In an embodiment $R^d$ is halogen, hydroxy and halo $C_{1-6}$alkyl.

Particular $R^d$ groups include fluoro, hydroxy and trifluoromethyl.

Particular $R^c$ groups include piperazinyl, piperidinyl, cyclohexyl, fluoropiperidinyl, azetidinyl, pyrrolidinyl, hydroxycyclohexyl, tetrahydropyranyl, hydroxypiperidinyl, hydroxyazetidinyl and (trifluoromethyl)azetidinyl.

Specific $R^c$ groups include piperazin-1-yl, piperidin-4-yl, cyclohexyl, (3R)-piperidin-3-yl, (3S)-piperidin-3-yl, trans-3-fluoropiperidin-4-yl, cis-3-fluoropiperidin-4-yl, azetidin-3-yl, (3S)-pyrrolidin-3-yl, (3R)-pyrrolidin-3-yl, trans-4-hydroxycyclohexyl, tetrahydro-2H-pyran-4-yl, 4-hydroxypiperidin-1-yl, 3-hydroxyazetidin-1-yl, 4-hydroxycyclohexyl and 3-(trifluoromethyl)azetidin-3-yl.

In an embodiment when $R^d$ is a ring it is optionally substituted by one, two or three independently selected groups.

In an embodiment each of $R^v$ and $R^w$ is independently hydrogen, $C_{1-6}$alkyl or halo$C_{1-6}$alkyl.

In another embodiment one of $R^v$ and $R^w$ is hydrogen and the other hydrogen, $C_{1-6}$alkyl or halo$C_{1-6}$alkyl.

Particular $R^v$ groups include hydrogen, methyl and trifluoromethyl.

Specific $R^v$ groups include hydrogen, (R)-methyl, (S)-methyl and trifluoromethyl.

A particular $R^w$ group is hydrogen.

In an embodiment when $R^5$ is a ring it is optionally substituted by one, two or three independently selected groups.

In an embodiment when $R^6$ is a ring it is optionally substituted by one, two or three independently selected groups.

In an embodiment each of $R^5$ and $R^6$ is independently hydrogen, halogen or $C_{1-6}$alkyl.

In an embodiment $R^5$ is hydrogen or $C_{1-6}$alkyl.

Particular $R^5$ groups are hydrogen and methyl.

In an embodiment $R^6$ is hydrogen.

In an embodiment each of $R^5$ and $R^6$ is independently hydrogen or $C_{1-6}$alkyl.

In an embodiment when $R^7$ is a ring it is optionally substituted by one, two or three independently selected groups.

In an embodiment $R^7$ is hydrogen, $C_{1-6}$alkyl or halo $C_{1-6}$alkyl.

In an embodiment $R^7$ is hydrogen or halo$C_{1-6}$alkyl, for example fluoro$C_{1-6}$alkyl.

Particular $R^7$ groups are hydrogen and trifluoroethyl.

Specific $R^7$ groups include hydrogen and 2,2,2-trifluoroethyl.

In an embodiment each of $R^x$ and $R^y$ is independently hydrogen or $C_{1-6}$alkyl. In another embodiment each of $R^x$ and $R^y$ is hydrogen.

In an embodiment $R^z$ is hydrogen or $C_{1-4}$alkyl.

In an embodiment $R^z$ is hydrogen, methyl, ethyl or propyl.

In an embodiment:
a is 0; and
$R^3$ is hydrogen.

In another embodiment:
$R^5$ is hydrogen or $C_{1-6}$alkyl; and
$R^6$ is hydrogen.

In another embodiment:
a is 0;
each of $R^3$ and $R^6$ is hydrogen;
$R^5$ is hydrogen or $C_{1-6}$alkyl; and
$R^7$ is hydrogen, $C_{1-6}$alkyl or halo$C_{1-6}$alkyl.

The present invention also provides compounds of formula II:

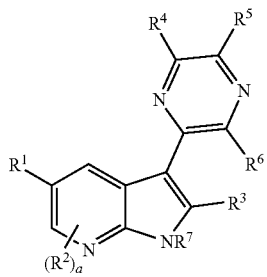

(II)

wherein:

a, $R^2$, $R^3$, $R^4$, $R^5$, $R^6$ and $R^7$ are as defined above;

$R^1$ is azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O, and S, not more than one heteroatom of which is O or S, a 6 membered heteroaromatic ring containing 1, 2 or 3 N atoms or a 7-15 membered unsaturated, partially saturated or saturated heterocyclic ring containing 1, 2, 3 or 4 heteroatoms independently selected from N, O and S; optionally substituted by one or more groups independently selected from $R^a$; and $R^a$ is as defined above;

or a pharmaceutically acceptable salt, stereoisomer or tautomer thereof.

The present invention also provides compounds of formula III:

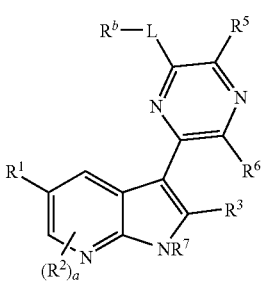

(III)

wherein:

a, L, $R^b$, $R^2$, $R^3$, $R^5$, $R^6$ and $R^7$ are as defined above;

$R^1$ is azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O, and S, not more than one heteroatom of which is O or S, a 6 membered heteroaromatic ring containing 1, 2 or 3 N atoms or a 7-15 membered unsaturated, partially saturated or saturated heterocyclic ring containing 1, 2, 3 or 4 heteroatoms independently selected from N, O and S; optionally substituted by one or more groups independently selected from $R^a$; and $R^a$ is as defined above;

or a pharmaceutically acceptable salt, stereoisomer or tautomer thereof.

The present invention also provides compounds of formula IV:

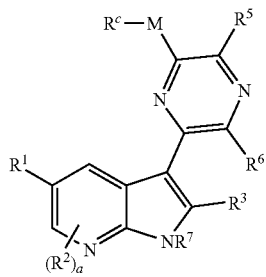

(IV)

wherein:

a, M, $R^c$, $R^2$, $R^3$, $R^5$, $R^6$ and $R^7$ are as defined above;

$R^1$ is azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O, and S, not more than one heteroatom of which is O or S, a 6 membered heteroaromatic ring containing 1, 2 or 3 N atoms or a 7-15 membered unsaturated, partially saturated or saturated heterocyclic ring containing 1, 2, 3 or 4 heteroatoms independently selected from N, O and S; optionally substituted by one or more groups independently selected from $R^a$; and $R^a$ is as defined above;

or a pharmaceutically acceptable salt, stereoisomer or tautomer thereof.

The preferred identities with reference to formulae II, III and IV are as defined previously for formula I mutatis mutandis.

The present invention also includes within its scope N-oxides of the compounds of formula I above. In general, such N-oxides may be formed on any available nitrogen atom. The N-oxides may be formed by conventional means, such as reacting the compound of formula I with oxone in the presence of wet alumina.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula I and salts thereof, for example, hydrates.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted. If the ring system is bicyclic, it is intended that the bond be attached to any of the suitable atoms on either ring of the bicyclic moiety.

The compounds may exist in different isomeric forms, all of which are encompassed by the present invention.

The compounds may exist in a number of different polymorphic forms.

When any variable (e.g. $R^2$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

In an embodiment one or more hydrogen atoms in the compounds of the present invention may be replaced by Deuterium.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" should be taken to be equivalent to the phrase "unsubstituted or substituted with one or more substituents" and in such cases the preferred embodiment will have from zero to three substituents. More particularly, there are zero to two substituents. A substituent on a saturated, partially saturated or unsaturated heterocycle can be attached at any substitutable position.

As used herein, "alkyl" is intended to include both branched, straight-chain and cyclic saturated aliphatic hydrocarbon groups having the specified number of carbon atoms. For example, "$C_{1-6}$alkyl" is defined to include groups having 1, 2, 3, 4, 5 or 6 carbons in a linear, branched or cyclic arrangement. For example, "$C_{1-6}$alkyl" specifically includes methyl, ethyl, n-propyl, i-propyl, n-butyl, t-butyl, i-butyl, pentyl, hexyl, cyclopropyl, cyclobutyl, cyclopentyl and cyclohexyl, cyclopropylmethyl, cyclobutylmethyl and so on. Preferred alkyl groups are methyl ethyl and cycloalkylmethyl, especially methyl and ethyl. The term "cycloalkyl" means a monocyclic, bicyclic or polycyclic saturated aliphatic hydrocarbon group having the specified number of carbon atoms. For example, "$C_{3-10}$cycloalkyl" is defined to include groups having 3, 4, 5, 6, 7, 8, 9 or 10 carbons and includes cyclopropyl, cyclopropylmethyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl, 7,7-dimethylbicyclo[2.2.1]heptyl and so on. Preferred cycloalkyl groups are cyclopropyl, cyclopropylmethyl, cyclobutyl, cyclopentyl and cyclohexyl.

As used herein, the term "$C_{2-6}$alkenyl" refers to a non-aromatic hydrocarbon radical, straight or branched, containing from 2 to 6 carbon atoms and at least one carbon to carbon double bond. Preferably one carbon to carbon double bond is present, and up to four non-aromatic carbon-carbon double bonds may be present. Alkenyl groups include ethenyl, propenyl, butenyl and 2-methylbutenyl. Preferred alkenyl groups include ethenyl and propenyl.

As used herein, the term "$C_{2-6}$alkynyl" refers to a hydrocarbon radical straight or branched, containing from 2 to 6 carbon atoms and at least one carbon to carbon triple bond. Up to three carbon-carbon triple bonds may be present. Alkynyl groups include ethynyl, propynyl, butynyl, 3-methylbutynyl and so on. Preferred alkynyl groups include ethynyl and propynyl "Alkoxy" represents an alkyl group of indicated number of carbon atoms attached through an oxygen bridge. "Alkoxy" therefore encompasses the definitions of alkyl above. Examples of suitable alkoxy groups include methoxy, ethoxy, n-propoxy, i-propoxy, n-butoxy, s-butoxy and t-butoxy. The preferred alkoxy groups are methoxy and ethoxy. The term '$C_{6-10}$aryloxy' can be construed analogously, and an example of this group is phenoxy.

The terms "halo$C_{1-6}$alkyl" and "halo$C_{1-6}$alkoxy" mean a $C_{1-6}$alkyl or $C_{1-6}$alkoxy group in which one or more (in particular, 1 to 3) hydrogen atoms have been replaced by halogen atoms, especially fluorine or chlorine atoms. Preferred are fluoro$C_{1-6}$alkyl and fluoro$C_{1-6}$alkoxy groups, in particular fluoro$C_{1-3}$alkyl and fluoro$C_{1-3}$alkoxy groups, for example, $CF_3$, $CHF_2$, $CH_2F$, $CH_2CH_2F$, $CH_2CHF_2$, $CH_2CF_3$, $OCF_3$, $OCHF_2$, $OCH_2F$, $OCH_2CH_2F$, $OCH_2CHF_2$ or $OCH_2CF_3$, and most especially $CF_3$, $OCF_3$ and $OCHF_2$.

As used herein, the term "hydroxy$C_{1-6}$alkyl" means a $C_{1-6}$alkyl group in which one or more (in particular, 1 to 3) hydrogen atoms have been replaced by hydroxy groups. Preferred are $CH_2OH$, $CH_2CHOH$ and $CHOHCH_3$.

The term "$C_{1-6}$alkylcarbonyl" or "$C_{1-6}$alkoxycarbonyl" denotes a $C_{1-6}$alkyl or $C_{1-6}$alkoxy radical, respectively, attached via a carbonyl (C=O) radical. Suitable examples of $C_{1-6}$alkylcarbonyl groups include methylcarbonyl, ethylcarbonyl, propylcarbonyl, isopropylcarbonyl and tert-butylcarbonyl. Examples of $C_{1-6}$alkoxycarbonyl include methoxycarbonyl, ethoxycarbonyl, propoxycarbonyl, isopropoxycarbonyl and tert-butoxycarbonyl. The term '$C_{6-10}$arylcarbonyl' can be construed analogously, and an example of this group is benzoyl.

The rings present in the compounds of this invention may be monocyclic or multicyclic, particularly bicyclic. The multicyclic rings may be fused or spiro linked.

As used herein, "$C_{6-10}$aryl" is intended to mean any stable monocyclic or bicyclic carbon ring of 6 to 10 atoms, wherein at least one ring is aromatic. Examples of such aryl elements include phenyl, naphthyl, tetrahydronaphthyl, indanyl and tetrahydrobenzo[7]annulene. The preferred aryl group is phenyl or naphthyl, especially phenyl.

7-15 membered heterocycles include 7, 8, 9, 10, 11, 12, 13, 14 and 15 membered heterocycles.

Examples of particular heterocycles of this invention are benzimidazolyl, benzofurandionyl, benzofuranyl, benzofurazanyl, benzopyrazolyl, benzotriazolyl, benzothienyl, benzoxazolyl, benzoxazolonyl, benzothiazolyl, benzothiadiazolyl, benzodioxolyl, benzoxadiazolyl, benzoisoxazolyl, benzoisothiazolyl, chromenyl, chromanyl, isochromanyl, carbazolyl, carbolinyl, cinnolinyl, epoxidyl, furyl, furazanyl, imidazolyl, indolinyl, indolyl, indolizinyl, indolinyl, isoindolinyl, indazolyl, isobenzofuranyl, isoindolyl, isoquinolyl, isothiazolyl, isoxazolyl, naphthpyridinyl, oxadiazolyl, oxazolyl, oxazolinyl, isoxazolinyl, oxetanyl, purinyl, pyranyl, pyrazinyl, pyrazolyl, pyridazinyl, pyridopyridinyl, pyridazinyl, pyridinyl, pyrimidinyl, triazinyl, tetrazinyl, pyrrolyl, quinazolinyl, quinolinyl, quinoxalinyl, quinolizinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidyl, pyridin-2-onyl, pyrrolidinyl, imidazolinyl, imidazolidinyl, pyrazolinyl, pyrrolinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydroisoquinolinyl, dihydrotetrazolyl, dihydrothiadiazolyl, dihydrothiazolyl, dihydrothienyl, dihydrotriazolyl, dihydroazetidinyl, dihydroisochromenyl, dihydrochromenyl, dihydroimidazolonyl, dihydrotriazolonyl, dihydrobenzodioxinyl, dihydrothiazolopyrimidinyl, dihydroimidazopyrazinyl, methylenedioxybenzoyl, tetrahydrofuranyl, tetrahydrothienyl, tetrahydroquinolinyl, thiazolidinonyl, imidazolonyl, isoindolinonyl, octahydroquinolizinyl, octahydroisoindolyl, imidazopyridinyl, azabicycloheptanyl, chromenonyl, triazolopyrimidinyl, dihydrobenzoxazinyl, thiazolotriazolyl, azoniabicycloheptanyl, azoniabicyclooctanyl, phthalazinyl, naphthyridinyl, quinazolinyl, pteridinyl, dihydroquinazolinyl, dihydrophthalazinyl, benzisoxazolyl, tetrahydronaphthyridinyl, dibenzo[b,d]furanyl, dihydrobenzothiazolyl, imidazothiazolyl, tetrahydroindazolyl, tetrahydrobenzothienyl, hexahydronaphthyridinyl, tetrahydroimidazopyridinyl, tetrahydroimidazopyrazinyl, pyrrolopyridinyl, azoniaspiro[5.5]undecanyl, azepanyl, octahydroindolizinyl, 1'2'-dihydrospirocyclohexane-1,3'-indolyl, azoniabicyclo[3.1.0]hexanyl, diazoniaspiro[4.4]nonanyl, hexahydropyrrolo[3,4-b]pyrrolyl, oxaazoniabicyclo[2.2.1]heptanyl, diazoniaspriro[5.5]undecanyl, diazoniaspiro[3.3]heptanyl, diazoniaspiro[3.5]nonanyl, diazoniaspiro[4.5]decanyl, octahydropyrrolo[3,4-c]pyrrolyl, octahydropyrrolo[3,4-b]pyrrolyl, octahydrocyclopenta[c]pyrrolyl, dihydroindolyl, azoniaspiro[4.5]decanyl, diazoniabicyclo[2.2.2]octanyl, diazoniabicyclo[2.2.1]heptanyl, diazoniabicyclo[3.2.1]octanyl, diazoniabicyclo[2.2.1]heptanyl, azoniabicyclo[3.1.0]hexanyl, tetrahydrothiophenyl, oxaazoniaspiro[4.5]decanyl, oxazepanyl and N-oxides thereof. Attachment of a heterocyclyl substituent can occur via a carbon atom or via a heteroatom.

Preferred 5 or 6 membered saturated or partially saturated heterocycles are pyrrolidinyl, piperidinyl, piperazinyl, morpholinyl, tetrahydrofuran, thiomorpholinyl, dihydroimidazolyl and tetrahydropyranyl.

A preferred 7 membered saturated heterocycle is diazepanyl, azepanyl and oxazepanyl.

Preferred 5 membered heteroaromatic rings are thienyl, thiazolyl, pyrazolyl, isoxazolyl, isothiazolyl, imidazolyl, thiadiazolyl, oxazolyl, oxadiazolyl, triazolyl, tetrazolyl, furyl and pyrrolyl.

Preferred 6 membered heteraromatic rings are pyridinyl, pyrimidinyl, pyridazinyl and pyrazinyl.

Preferred 7-15 membered partially saturated or unsaturated heterocyclic rings are tetrahydroquinolinyl, quinolinyl, indolyl, imidazopyridinyl, benzothiazolyl, quinoxalinyl, benzothiadiazolyl, benzoxazolyl, dihydrobenzodioxinyl, benzotriazolyl, benzodioxolyl, dihydroisoindolyl, dihydroindolyl, tetrahydroisoquinolinyl, isoquinolinyl, benzoisothiazolyl, dihydroimidazopyrazinyl, benzothienyl, benzoxadiazolyl, thiazolotriazolyl, dihydrothiazolopyrimidinyl, dihydrobenzoxazinyl, dihydrobenzofuranyl, benzimidazolyl, benzofuranyl, dihydrobenzoxazolyl, dihydroquinazolinyl, dihydrophthalazinyl, indazolyl, benzisoxazolyl, tetrahydronaphthyridinyl, triazolopyrimidinyl, dibenzo[b,d]furanyl, naphthyridinyl, dihydroquinolinyl, dihydroisochromenyl, dihydrochromenyl, dihydrobenzothiazolyl, imidazothiazolyl, tetrahydroindazolyl, tetrahydrobenzothienyl, hexahydronaphthyridinyl, tetrahydroimidazopyridinyl, tetrahydroimidazopyrazinyl, pyrrolopyridinyl, quinazolinyl, indolizinyl, azoniaspiro[5.5]undecanyl, azepanyl, octahydroindolizinyl, 1'2'-dihydrospirocyclohexane-1,3'-indolyl, octahydroisoindolyl, azoniabicyclo[3.1.0]hexanyl, diazoniaspiro[4.4]nonanyl, hexahydropyrrolo[3,4-b]pyrrolyl, oxaazoniabicyclo[2.2.1]heptanyl, diazoniaspriro[5.5]undecanyl, diazoniaspiro[3.3]heptanyl, diazoniaspiro[3.5]nonanyl, diazoniaspiro[4.5]decanyl, octahydropyrrolo[3,4-c]pyrrolyl, octahydropyrrolo[3,4-b]pyrrolyl, octahydrocyclopenta[c]pyrrolyl, dihydroindolyl, azoniaspiro[4.5]decanyl, diazoniabicyclo[2.2.2]octanyl, diazoniabicyclo[2.2.1]heptanyl, diazoniabicyclo[3.2.1]octanyl, diazoniabicyclo[2.2.1]heptanyl, azoniabicyclo[3.1.0]hexanyl, tetrahydrothiophenyl, oxaazoniaspiro[4.5]decanyl and oxazepanyl.

As used herein, the term "halogen" refers to fluorine, chlorine, bromine and iodine, of which fluorine and chlorine are preferred.

Particular compounds within the scope of the present invention are:
5-(1-methyl-1H-pyrazol-4-yl)-3-(6-piperazin-1-ylpyrazin-2-yl)-1H-pyrrolo[2,3-b]pyridine;
5-(1-methyl-1H-pyrazol-4-yl)-3-[6-(piperidin-4-yloxy)pyrazin-2-yl]-1H-pyrrolo[2,3-b]pyridine;
3-[6-(cyclohexyloxy)pyrazin-2-yl]-5-(1-methyl-1H-pyrazol-4-yl)-1H-pyrrolo[2,3-b]pyridine;
N-methyl-6-[5-(1-methyl-1H-pyrazol-4-yl)-1H-pyrrolo[2,3-b]pyridin-3-yl]-N-piperidin-4-ylpyrazin-2-amine;
3-[6-(piperidin-4-yloxy)pyrazin-2-yl]-5-(1H-pyrazol-4-yl)-1H-pyrrolo[2,3-b]pyridine;
3-{6-[(3R)-piperidin-3-yloxy]pyrazin-2-yl}-5-(1H-pyrazol-4-yl)-1H-pyrrolo[2,3-b]pyridine;
3-{6-[(3S)-piperidin-3-yloxy]pyrazin-2-yl}-5-(1H-pyrazol-4-yl)-1H-pyrrolo[2,3-b]pyridine;
trans-3-{6-[(3-fluoropiperidin-4-yl)oxy]pyrazin-2-yl}-5-(1H-pyrazol-4-yl)-1H-pyrrolo[2,3-b]pyridine;
cis-3-{6-[(3-fluoropiperidin-4-yl)oxy]pyrazin-2-yl}-5-(1H-pyrazol-4-yl)-1H-pyrrolo[2,3-b]pyridine;
3-[6-(azetidine-3-yloxy)pyrazin-2-yl]-5-(1H-pyrazol-4-yl)-1H-pyrrolo[2,3-b]pyridine;
5-(1H-pyrazol-4-yl)-3-{6-[(3S)-pyrrolidin-3-yloxy]pyrazin-2-yl}-1H-pyrrolo[2,3-b]pyridine;
(2S)-1-({6-[5-(1H-pyrazol-4-yl)-1H-pyrrolo[2,3-b]pyridin-3-yl]pyrazin-2-yl}oxy)propan-2-amine;
(2S)-2-({6-[5-(1H-pyrazol-4-yl)-1H-pyrrolo[2,3-b]pyridin-3-yl]pyrazin-2-yl}oxy)propan-1-amine;

5-(1H-pyrazol-4-yl)-3-{6-[(3R)-pyrrolidin-3-yloxy]
    pyrazin-2-yl-1H-pyrrolo[2,3-b]pyridine;
(2R)-1-({6-[5-(1H-pyrazol-4-yl)-1H-pyrrolo[2,3-b]pyridin-
    3-yl]pyrazin-2-yl}oxy)propan-2-amine;
(2R)-2-({6-[5-(1H-pyrazol-4-yl)-1H-pyrrolo[2,3-b]pyridin-
    3-yl]pyrazin-2-yl}oxy)propan-1-amine;
Trans-4-({6-[5-(1H-pyrazol-4-yl)-1H-pyrrolo[2,3-b]pyri-
    din-3-yl]pyrazin-2-yl}amino)cyclohexanol;
6-[5-(1H-pyrazol-4-yl)-1H-pyrrolo[2,3-b]pyridin-3-yl-N-
    (tetrahydro-2H-pyran-5-yl)pyrazin-2-amine;
1-{6-[5-(1H-pyrazol-4-yl)-1H-pyrrolo[2,3-b]pyridin-3-yl]
    pyrazin-2-yl}piperidin-4-ol;
2-({6-[5-(1H-pyrazol-4-yl)-1H-pyrrolo[2,3-b]pyridin-3-yl]
    pyrazin-2-yl}amino)ehtanol;
1-{6-[5-(1H-pyrazol-4-yl)-1H-pyrrolo[2,3-b]pyridin-3-yl]
    pyrazin-2-yl}azetidin-3-ol;
3-({6-[5-(1H-pyrazol-4-yl)-1H-pyrrolo[2,3-b]pyridin-3-
    yl}pyrazin-2-yl)amino)propan-1-ol;
4-({6-[5-(1H-pyrazol-4-yl)-1H-pyrrolo[2,3-b]pyridin-3-yl]
    pyrazin-2-yl}oxy)cyclohexanol;
5-(1-ethyl-1H-pyrazol-4-yl)-3-[6-(piperidin-4-yloxy)
    pyrazin-2-yl]-1H-pyrrolo[2,3-b]pyridine;
5-[1-(cyclopropylmethyl)-1H-pyrazol-4-yl]-3-[6-(piperidin-
    4-yloxy)pyrazin-2-yl]-1H-pyrrolo[2,3-b]pyridine;
2-(4-{3[-[6-(piperidin-4-yloxy)pyrazin-2-yl]-1H-pyrrolo[2,
    3-b]pyridine-5-yl}-1H-pyrazol-1-yl)ethanol;
3-[6-(piperidin-4-yloxy)pyrazin-2-yl]-5-[1-(2,2,2-trifluoro-
    ethyl)-1H-pyrazol-4-yl]-1H-pyrrolo[2,3-b]pyridine;
3-[6-(piperidin-4-yloxy)pyrazin-2-yl]-1-(2,2,2-trifluoroet-
    hyl)-5-[1-(2,2,2-trifluoroethyl)-1H-pyrazol-4-yl]-1H-pyr-
    rolo[2,3-b]pyridine;
5-(1H-pyrazol-4-yl)-3-(6-{[3-(trifluoromethypazetidin-3-
    yl]oxy}pyrazin-2-yl]-1H-pyrrolo[2,3-b]pyridine;
3,3,3-trifluoro-2-({6-[5-(1H-pyrazol-4-yl)-1H-pyrrolo[2,3-
    b]pyridin-3-yl]pyrazin-2-yl}oxy)propan-1-amine;
N-ethyl-N-piperidin-4-yl-6-[5-(1H-pyrazol-4-yl)-1H-pyr-
    rolo[2,3-b]pyridin-3-yl]pyrazin-2-amine;
N-piperidin-4-yl-N-propyl-6-[5-(1H-pyrazol-4-yl)-1H-pyr-
    rolo[2,3-b]pyridin-3-yl]pyrazin-2-amine;
3-[5-methyl-6-(piperidin-4-yloxy)pyrazin-2-yl]-5-(1H-
    pyrazol-4-yl)-1H-pyrrolo[2,3-b]pyridine;
N-[2-({6-[5-(1H-pyrazol-4-yl)-1H-pyrrolo[2,3-b]pyridin-3-
    yl]pyrazin-2-yl}oxy)ethyl]cyclohexanamine;
    and pharmaceutically acceptable salts, stereoisomers and
tautomers thereof.

Included in the instant invention is the free form of compounds of the instant invention, as well as the pharmaceutically acceptable salts and stereoisomers thereof. Some of the isolated specific compounds exemplified herein are the protonated salts of amine compounds. The term "free form" refers to the amine compounds in non-salt form. The encompassed pharmaceutically acceptable salts not only include the isolated salts exemplified for the specific compounds described herein, but also all the typical pharmaceutically acceptable salts of the free form of compounds of the instant invention. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic (TFA) and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977: 66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The compounds of the invention can be used in a method of treatment of the human or animal body by therapy.

The present invention provides compounds for use in the treatment or prevention of any one or more of the conditions described herein.

Thus, the present invention provides compounds for use in the treatment or prevention of conditions which can be ameliorated by the inhibition of JAK kinases and/or PDK1.

The present invention provides a compound of formula I for use in the manufacture of a medicament for the treatment or prevention of conditions which can be ameliorated by the inhibition of JAK.

The present invention also provides a method for the treatment or prevention of conditions which can be ameliorated by the inhibition of JAK, which method comprises administration to a patient in need thereof of an effective amount of a compound of formula I or a composition comprising a compound of formula I.

The present invention also provides a compound of formula I for use in the manufacture of a medicament for the treatment or prevention of conditions which can be ameliorated by the inhibition of PDK1.

The present invention also provides a method for the treatment or prevention of conditions which can be ameliorated by the inhibition of PDK1, which method comprises administration to a patient in need thereof of an effective amount of a compound of formula I or a composition comprising a compound of formula I.

The compounds of the present invention are inhibitors of JAK and/or PDK1, and are therefore useful to treat or prevent myeloproliferative disorders or cancer in mammals, preferably humans.

An embodiment of the invention provides a method for inhibiting JAK1 tyrosine kinase, comprising administering to the mammal a therapeutically effective amount of any of the compounds or any of the pharmaceutical compositions described above.

An embodiment of the invention provides a method for inhibiting JAK2 tyrosine kinase, comprising administering to the mammal a therapeutically effective amount of any of the compounds or any of the pharmaceutical compositions described above.

An embodiment of the invention provides a method for inhibiting wild type or mutant JAK2 tyrosine kinase, comprising administering to the mammal a therapeutically effective amount of any of the compounds or any of the pharmaceutical compositions described above.

An embodiment of the invention provides a method for inhibiting JAK2V617F tyrosine kinase, comprising administering to the mammal a therapeutically effective amount of any of the compounds or any of the pharmaceutical compositions described above.

The compounds, compositions and methods provided herein are particularly deemed useful for the treatment of myeloproliferative disorder(s). Myeloproliferative disorders that may be treated include polycythemia vera (PV), essential thrombocythemia (ET), myeloid metaplasia with myelofibrosis (MMM), chronic myelogenous leukemia (CML), myelomonocytic leukemia (CMML), hypereosinophilic syndrome (HES), juvenile myelomonocytic leukemia (JMML), and systemic mast cell disease (SMCD).

It is known in the literature that inhibitors of JAK2 are useful in the treatment and/or prevention of myeloproliferative disorders. See, e.g., Tefferi, A. and Gilliland, D. G. *Mayo Clin. Proc.* 80(7): 947-958 (2005); Fernandez-Luna, J. L. et al. *Haematologica* 83(2): 97-98 (1998); Harrison, C. N. *Br. J. Haematol.* 130(2): 153-165 (2005); *Leukemia* (2005) 19, 1843-1844; and Tefferi, A. and Barbui, T. *Mayo Clin. Proc.* 80(9): 1220-1232 (2005).

The compounds, compositions and methods provided herein are also deemed useful for the treatment of cancer. Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma; and Adrenal glands: neuroblastoma. Thus, the term "cancerous cell" as provided herein, includes a cell afflicted by any one of the above-identified conditions.

Thus, the present invention provides a compound of formula I for use in the manufacture of a medicament for the treatment or prevention of cancer.

The present invention also provides a method for the treatment or prevention of cancer, which method comprises administration to a patient in need thereof of an effective amount of a compound of formula I or a composition comprising a compound of formula I.

The compounds, compositions and methods of the invention may also be useful in treating the following disease states: keloids and psoriasis.

Cancers that may be treated by the compounds, compositions and methods of the invention include, but are not limited to: breast, prostate, colon, colorectal, lung, brain, testicular, stomach, pancrease, skin, small intestine, large intestine, throat, head and neck, oral, bone, liver, bladder, kidney, thyroid and blood.

Cancers that may be treated by the compounds, compositions and methods of the invention include: breast, prostate, colon, ovarian, colorectal and lung (non-small cell lung).

Cancers that may be treated by the compounds, compositions and methods of the invention include: breast, colon, colorectal and lung.

Cancers that may be treated by the compounds, compositions and methods of the invention include: lymphoma and leukemia.

Cancers that may be treated by the compounds, composition and methods of the invention include: ovarian, pancreatic, breast and prostate cancer.

The compounds of the instant invention are also inhibitors of the activity of PDK1 and are thus useful in the treatment of cancer, in particular cancers associated with deregulated activity of the PTEN/PI3K pathway including, but not limited to PTEN loss of function mutations and receptor tyrosine kinase gain of function mutations. Such cancers include, but are not limited to, ovarian, pancreatic, breast and prostate cancer, as well as cancers (including glioblastoma) where the tumor suppressor PTEN is mutated. See, Feldman, Richard I., et al., "Novel Small Molecule Inhibitors of 3-Phosphoinositide-dependent Kinase-1," *The Journal of Biological Chemistry*, Vol. 280, No. 20, Issue of May 20, pp. 19867-19874, 2005.

PDK1 signaling regulates multiple critical steps in angiogenesis. See, Mora, Alfonso et al., "PDK1, the master regulator of AGC kinase signal transduction," *Seminars in Cell & Developmental Biology* 15 (2004) 161-170. The utility of angiogenesis inhibitors in the treatment of cancer is known in the literature, see J. Rak et al. *Cancer Research*, 55:4575-4580, 1995 and Dredge et al., *Expert Opin. Biol. Ther.* (2002) 2(8):953-966, for example. The role of angiogenesis in cancer has been shown in numerous types of cancer and tissues: breast carcinoma (G. Gasparini and A. L. Harris, *J. Clin. Oncol.*, 1995, 13:765-782; M. Toi et al., *Japan. J. Cancer Res.*, 1994, 85:1045-1049); bladder carcinomas (A. J. Dickinson et al., *Br. J. Urool.*, 1994, 74:762-766); colon carcinomas (L. M. Ellis et al., *Surgery*, 1996, 120(5):871-878); and oral cavity tumors (J. K. Williams et al., *Am. J. Surg.*, 1994, 168:373-380). Other cancers include, advanced tumors, hairy cell leukemia, melanoma, advanced head and neck, metastatic renal cell, non-Hodgkin's lymphoma, metastatic breast, breast adenocarcinoma, advanced melanoma, pancreatic, gastric, glioblastoma, lung, ovarian, non-small cell lung, prostate, small cell lung, renal cell carcinoma, various solid tumors, multiple myeloma, metastatic prostate, malignant glioma, renal cancer, lymphoma, refractory metastatic disease, refractory multiple myeloma, cervical cancer, Karposi's sarcoma, recurrent anaplastic glioma, and metastatic colon cancer (Dredge et al., *Expert Opin. Biol. Ther.* (2002) 2(8): 953-966). Thus, the PDK1 inhibitors disclosed in the instant application are also useful in the treatment of these angiogenesis related cancers.

Tumors which have undergone neovascularization show an increased potential for metastasis. In fact, angiogenesis is essential for tumor growth and metastasis. (S. P. Cunningham, et al., *Can. Research*, 61: 3206-3211 (2001)). The PDK1 inhibitors disclosed in the present application are therefore also useful to prevent or decrease tumor cell metastasis.

Further included within the scope of the invention is a method of treating or preventing a disease in which angiogenesis is implicated, which is comprised of administering to a mammal in need of such treatment a therapeutically effective amount of a compound of the present invention. Ocular neovascular diseases are an example of conditions where much of the resulting tissue damage can be attributed to aberrant infiltration of blood vessels in the eye (see WO 00/30651, published 2 Jun. 2000). The undesirable infiltration can be triggered by ischemic retinopathy, such as that resulting from diabetic retinopathy, retinopathy of prematurity, retinal vein occlusions, etc., or by degenerative diseases, such as the choroidal neovascularization observed in age-related macular degeneration. Inhibiting the growth of blood vessels by administration of the present compounds would therefore prevent the infiltration of blood vessels and prevent or treat diseases where angiogenesis is implicated, such as ocular diseases like retinal vascularization, diabetic retinopathy, age-related macular degeneration, and the like.

Further included within the scope of the invention is a method of treating or preventing a non-malignant disease in which angiogenesis is implicated, including but not limited to: ocular diseases (such as, retinal vascularization, diabetic retinopathy and age-related macular degeneration), atherosclerosis, arthritis, psoriasis, obesity and Alzheimer's disease (Dredge et al., *Expert Opin. Biol. Ther.* (2002) 2(8):953-966). In another embodiment, a method of treating or preventing a disease in which angiogenesis is implicated includes: ocular diseases (such as, retinal vascularization, diabetic retinopathy and age-related macular degeneration), atherosclerosis, arthritis and psoriasis.

An embodiment of the invention provides a method for inhibiting PDK1, comprising administering to the mammal a therapeutically effective amount of any of the compounds or any of the pharmaceutical compositions described above.

Further included within the scope of the invention is a method of treating hyperproliferative disorders such as restenosis, inflammation, autoimmune diseases and allergy/asthma.

Further included within the scope of the instant invention is the use of the instant compounds to coat stents and therefore the use of the instant compounds on coated stents for the treatment and/or prevention of restenosis (WO03/032809).

Further included within the scope of the instant invention is the use of the instant compounds for the treatment and/or prevention of osteoarthritis (WO03/035048).

Further included within the scope of the invention is a method of treating hypoinsulinism.

An embodiment of the invention provides a method for inhibiting JAK3 tyrosine kinase, comprising administering to the mammal a therapeutically effective amount of any of the compounds or any of the pharmaceutical compositions described above.

An embodiment of the invention provides a method for inhibiting TYK2 tyrosine kinase, comprising administering to the mammal a therapeutically effective amount of any of the compounds or any of the pharmaceutical compositions described above.

Exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone loss, bone resorption, bone fractures, metastatic bone disease and/or disorders related to cathepsin functioning. Still further exemplifying the invention is the use of any of the compounds described above in the preparation of a medicament for the treatment and/or prevention of hypertension.

The compounds of this invention may be administered to mammals, preferably humans, either alone or in combination with pharmaceutically acceptable carriers, excipients, diluents, adjuvants, fillers, buffers, stabilisers, preservatives, lubricants, in a pharmaceutical composition, according to standard pharmaceutical practice.

The compounds of this invention may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, (e.g. by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal); and by implant of a depot (e.g. subcutaneously or intramuscularly).

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutang, gibbon), or a human.

The invention also provides pharmaceutical compositions comprising one or more compounds of this invention and a pharmaceutically acceptable carrier. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection.

Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CARD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the instant invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compounds of the instant invention are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

When a compound according to this invention is administered into a subject, the selected dosage level will depend on a variety of factors including, but not limited to, the activity of the particular compound, the severity of the individuals symptoms, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In an embodiment, a suitable amount of an inhibitor of JAK2 is administered to a mammal undergoing treatment for cancer. Administration occurs in an amount of inhibitor of between about 0.1 mg/kg of body weight to about 60 mg/kg of body weight per day, or between 0.5 mg/kg of body weight to about 40 mg/kg of body weight per day. Another therapeutic dosage that comprises the instant composition includes from about 0.01 mg to about 1000 mg of inhibitor of JAK2. In another embodiment, the dosage comprises from about 1 mg to about 1000 mg of inhibitor of JAK2.

The instant compounds are also useful in combination with anti-cancer agents or chemotherapeutic agents.

The compounds of this invention may be useful as chemo- and radiosensitizers for cancer treatment. They are useful for the treatment of mammals who have previously undergone or are presently undergoing treatment for cancer. Such previous treatments include prior chemotherapy, radiation therapy, surgery or immunotherapy, such as cancer vaccines.

Thus, the present invention provides a combination of a compound of formula I and an anti-cancer agent for simultaneous, separate or sequential administration.

The present invention also provides a compound of formula I for use in the manufacture of a medicament for use as an adjunct in cancer therapy or for potentiating tumor cells for treatment with ionizing radiation or chemotherapeutic agents.

The present invention also provides a method of chemotherapy or radiotherapy, which method comprises administration to a patient in need thereof of an effective amount of a compound of formula I or a composition comprising a compound of formula I in combination with ionizing radiation or chemotherapeutic agents.

In combination therapy, the compounds of this invention can be administered prior to (e.g., 5 minutes, 15 minutes, 30 minutes, 45 minutes, 1 hour, 2 hours, 4 hours, 6 hours, 12 hours, 24 hours, 48, hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the other anticancer agent to a subject in need thereof. In various embodiments the instant compounds and another anticancer agent are administered 1 minute apart, 10 minutes apart, 30 minutes apart, less than 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart, or no more than 48 hours apart.

The compounds of this invention and the other anticancer agent can act additively or synergistically. A synergistic combination of the present compounds and another anticancer agent might allow the use of lower dosages of one or both of these agents and/or less frequent dosages of one or both of the instant compounds and other anticancer agents and/or to administer the agents less frequently can reduce any toxicity associated with the administration of the agents to a subject without reducing the efficacy of the agents in the treatment of cancer. In addition, a synergistic effect might result in the improved efficacy of these agents in the treatment of cancer and/or the reduction of any adverse or unwanted side effects associated with the use of either agent alone.

Examples of cancer agents or chemotherapeutic agents for use in combination with the compounds of the present invention can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: HDAC inhibitors, estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

Examples of "HDAC inhibitors" include suberoylanilide hydroxamic acid (SAHA), LAQ824, LBH589, PXD101, MS275, FK228, valproic acid, butyric acid and CI-994.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum(II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779 and Ariad's AP23573).

An example of a hypoxia activatable compound is tirapazamine.

Examples of proteosome inhibitors include but are not limited to lactacystin, bortezomib, epoxomicin and peptide aldehydes such as MG 132, MG 115, PSI and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5, 6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB, 8aa,9b)-9-[2-[N-[2-(dimethylamino)ethyl]-N-methylamino] ethyl]-5-[4-hydroxy-3,5-dimethoxyphenyl]-5,5a,6,8,8a,9-hexohydrofuro(3',l':6,7)naphtho(2,3-d)-1,3-dioxol-6-one, 2,3-(methylenedioxy)-5-methyl-7-hydroxy-8-methoxybenzo[c]-phenanthridinium, 6,9-bis[[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxarithen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, dimesna, non-camptothecin topoisomerase-1 inhibitors such as indolocarbazoles; and dual topoisomerase-1 and II inhibitors such as benzophenazines, XR 20 115761MLN 576 and benzopyridoindoles.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589, 485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (*PNAS*, Vol.

89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetylcarbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK11 and CHK12 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature*, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469), inhibitors of Raf kinase (for example BAY-43-9006), inhibitors of MEK (for example CI-1040 and PD-098059), inhibitors of mTOR (for example Wyeth CCI-779 and Ariad's AP23573), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 μM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344,991, 5,134,142, 5,380,738, 5,393,790, 5,466,823, 5,633,272 and 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof. Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1,1-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)pindolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods, for simultaneous, separate or sequential administration. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Opthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119: 709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenypethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with inhibitors of Akt. Such inhibitors include compounds described in, but not limited to, the following publications: WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469.

A compound of the instant invention may also be useful for treating or preventing cancer in combination with mTor inhibitors.

A compound of the instant invention may also be useful for treating or preventing cancer in combination with cMet inhibitors.

A compound of the instant invention may also be useful for treating or preventing cancer in combination with PARP inhibitors.

A compound of the instant invention may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosole®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATA (Vesanoid®); Uracil Mustard (Uracil Mustard Capsules®); valrubicin (Valstar®); vinblastine (Velban®); vincristine (Oncovin®); vinorelbine (Navelbine®); vorinostat (Zolinza®); and zoledronate (Zometa®). Further therapeutic agents which can be used in combination with the compounds of the instant invention include: bendamustine hydrochloride (Treanda®); ixabepilone (Ixempra®); lapatinib (Tykerb®); nilotinib hydrochloride monohydrate (Tasigna®); raloxifene hydrochloride (Evista®); and temsirolimus (Torisel®).

Thus, the scope of the instant invention encompasses the use of the instantly claimed compounds in combination with a second compound selected from: HDAC inhibitor, an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

Also included in the scope of the claims is a method of treating cancer that comprises administering a therapeutically effective amount of a compound of the instant invention in combination with radiation therapy and/or in combination with a second compound selected from: HDAC inhibitor, an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

The instant invention also includes a pharmaceutical composition useful for treating or preventing cancer that comprises a therapeutically effective amount of a compound of the instant invention and a second compound selected from: HDAC inhibitor, an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

All patents, publications and pending patent applications identified are hereby incorporated by reference.

The compounds of the present invention can be prepared according to the following procedures.

Abbreviations:

DMF (Dimethylformamide); Pd(PPh$_3$)$_4$ (Tetrakis(triphenylphosphine)palladium(0)); THF (Tetrahydrofuran); Pd$_2$(dba)$_3$ (Tris(dibenzylideneacetone)dipalladium(0)); PCy$_3$ (Tricyclohexylphosphine); PdCl$_2$(dppf)-CH$_2$Cl$_2$ adduct (1,1'-Bis(dipheylphosphino) ferrocene palladium(II) chloride); Et$_3$N (Triethylamine); nPrOH (nPropanol); MeOH (Methanol); EtOAc (Ethyl acetate); DCM (Dichloromethane); BOC$_2$O (di-tert-butyl dicarbonate); DMAP (4-Dimethylaminopyridine); TLC (Thin layer chromatography); LRMS (Low resolution mass spectrometry); TMSCl (Trimethylchlorosilane); DIAD (Diisopropyl azodicarboxylate); HPLC (High pressure liquid chromatography); DMSO (Dimethyl sulfoxide); NaHMDS (Sodium bis(trimethylsilyl) amide); and EtOH (Ethanol).

Compounds of formula I can be prepared by reacting a compound of formula IA with a compound of formula IB:

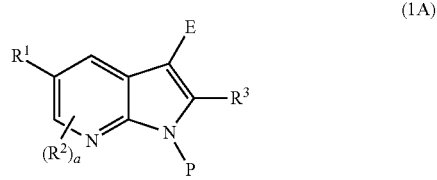

(1A)

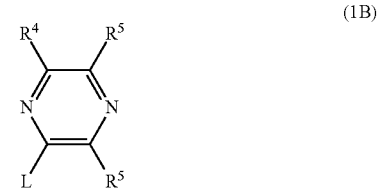

(1B)

wherein a, R$^1$, R$^2$, R$^3$, R$^4$, R$^5$ and R$^6$ are as defined above, B is a reagent such as organoboran, organostannane, organosilicon or Grignard, for example $^-$BF$_3$, P is a protecting group such as phenylsulfonyl and L is a leaving group such as halogen, for example chlorine. The reaction is generally carried out in the presence of a base such as Et$_3$N in a solvent such as nPrOH at about 100° C. A catalyst such as PdCl$_2$(dppf)-CH$_2$Cl$_2$ adduct may also be used.

Where the synthesis of intermediates and starting materials is not described, these compounds are commercially available or can be made from commercially available compounds by standard methods or by extension of the synthesis above, schemes and Examples herein.

Compounds of formula I may be converted to other compounds of formula I by known methods or by methods described in the synthesis above, schemes and Examples herein.

During any of the synthetic sequences described herein it may be necessary and/or desirable to protect sensitive or reactive groups on any of the molecules concerned. This may be achieved by means of conventional protecting groups, such as those described in *Protecting Groups in Organic Synthesis,* 3rd Edition, Greene, T. W. and Wuts, P. G. M.; Wiley Interscience, 1999 and Kocienski, P. J. *Protecting Groups,* Thieme, 1994. The protecting groups may be removed at a convenient subsequent stage using methods known from the art. For example, when the Boc (tert-butoxycarbonyl) or benzylcarbonyl protecting group is present, it may be removed by the addition of solvents such as TFA, DCM and/or MeCN at about room temperature. When a CBz (benzyloxycarbonyl) protecting group is present, the compound may be hydrogenated using standard methods, such as treating with a catalyst such as Pd/C, in a solvent such as methanol under a hydrogen atmosphere. EtOAc in the presence of HCl and 1,4-dioxane may also be added to remove the Boc protecting group, at about room temperature.

When the compounds of the present invention have chiral centres, the enantiomers may be separated from the racemic mixtures by standard separating methods such as using SFC.

The compounds of this invention were prepared according to the following schemes. All variables within the formulae are as defined above.

-continued

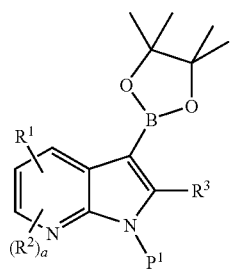

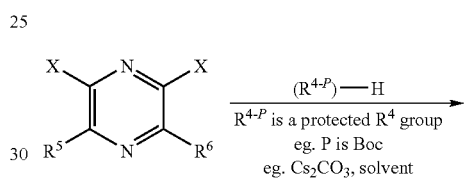

Scheme 1

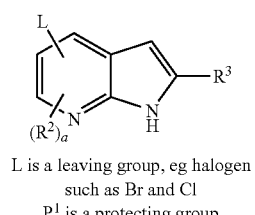

L is a leaving group, eg halogen such as Br and Cl
$P^1$ is a protecting group such as $PhSO_2$

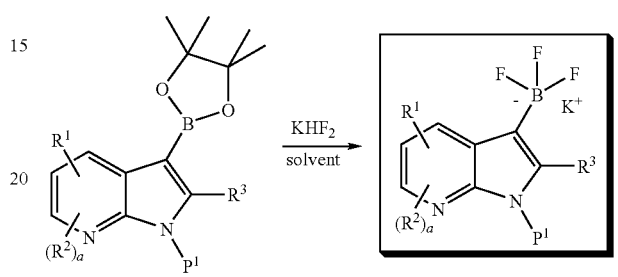

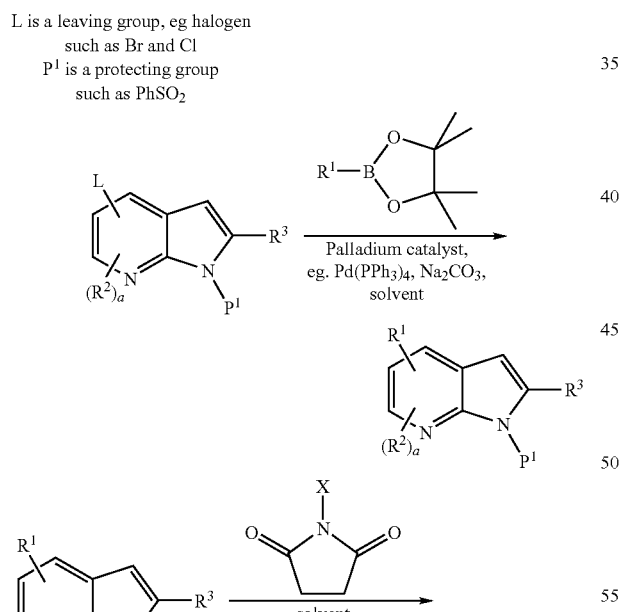

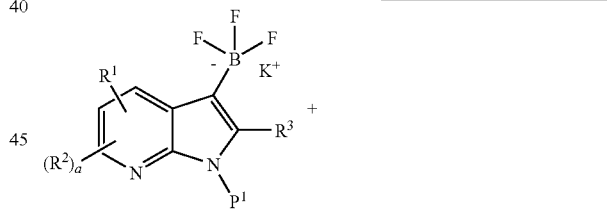

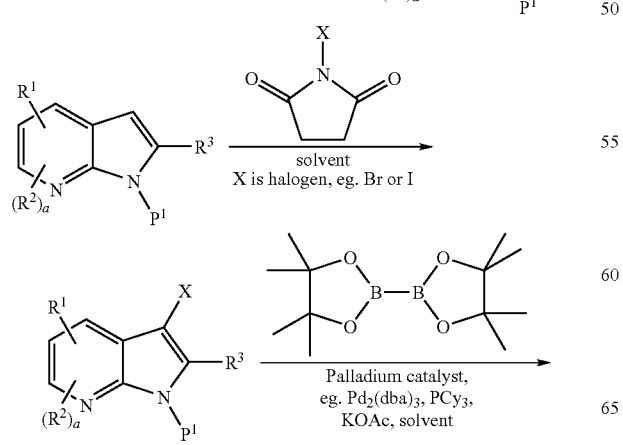

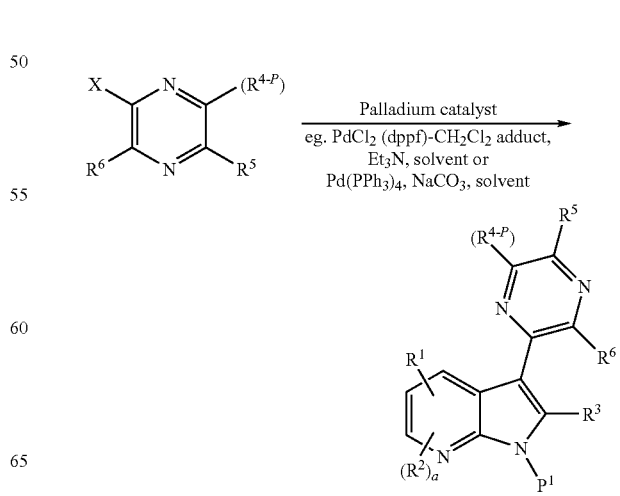

-continued

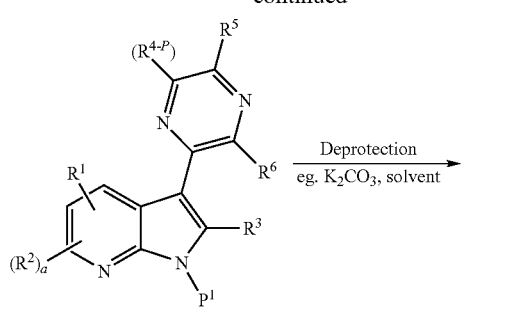

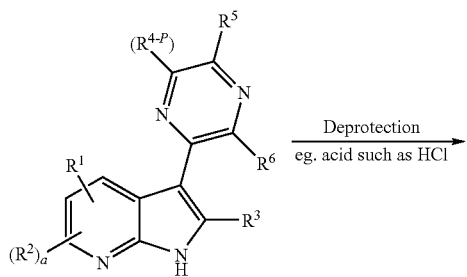

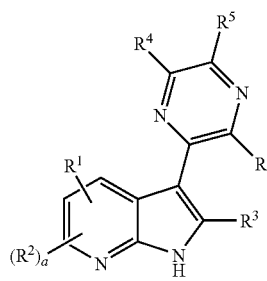

Scheme 2

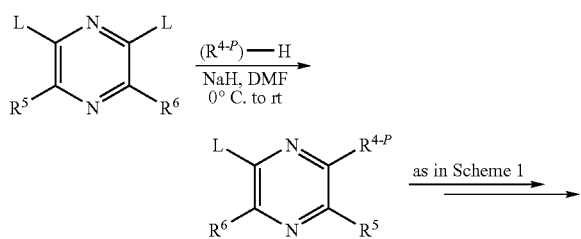

L is a leaving group, eg halogen such as Br and Cl

Scheme 3

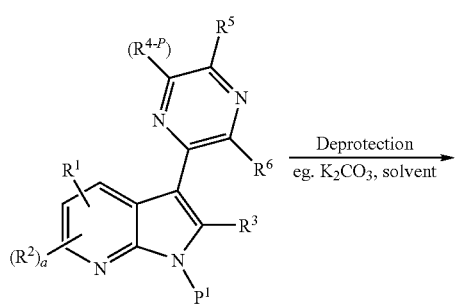

-continued

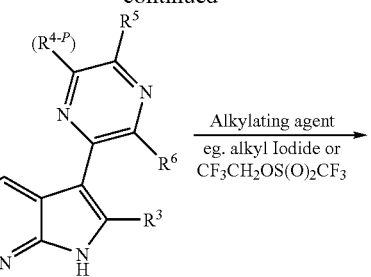

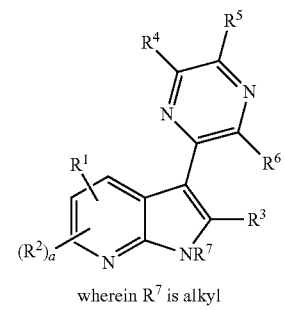

wherein $R^7$ is alkyl

Biological Assays

JAK2 Kinase Activity Inhibition Assay and Determination of $IC_{50}$

The kinase activity was measured using a modified version of the homogeneous time-resolved tyrosine kinase assay described in Park et al. *Anal. Biochem.* 269, 94-104 (1999).

The procedure for determining the potency of a compound to inhibit JAK2 kinase comprises the following steps:

1. prepare 3-fold serial diluted compound/inhibitor solutions in 100% (DMSO) at 20× of the final desired concentrations in a 96 well plate;
2. prepare a master reaction mix containing 6.67 mM $MgCl_2$, 133.3 mM NaCl, 66.7 mM Tris-HCl (pH 7.4), 0.13 mg/ml BSA, 2.67 mM dithiothreitol, 0.27 recombinant JAK2 and 666.7 nM biotinylated synthetic peptide substrate (biotin-ahx-EQEDEPEGDYFEWLE-$CONH_2$) (SEQ. ID.: 1);
3. in a black assay plate, add 2.5 μl compound/inhibitor (or DMSO) and 37.5 μl master reaction mix per well; initiate the kinase reaction by adding 10 μl of 75 μM MgATP per well, allow the reactions to proceed for 80 minutes at room temperate; (the final conditions for the reactions are: 50 nM JAK2 JH1 domain (Upstate), 2.0 μM substrate, 15 μM MgATP, 5 mM $MgCl_2$, 100 mM NaCl, 2 mM DTT, 0.1 mg/ml BSA, 50 mM Tris (pH 7.4) and 5% DMSO);
4. stop the kinase reaction with 50 μl of Stop/Detection buffer containing 10 mM EDTA, 25 mM HEPES, 0.1% TRITON X-100, 0.126 μg/ml Eu-chelate labeled anti-phosphotyrosine antibody PY20 (cat. # AD0067, PerkinElmer) and 45 μg/ml Streptavidin-allophycocyanin conjugate (cat. # PJ25S, Prozyme); and
5. read HTRF signals on a Victor reader (PerkinElmer) in HTRF mode after 60 minutes.

$IC_{50}$ was obtained by fitting the observed relationship between compound/inhibitor concentration and HTRF signal with a 4-parameter logistic equation.

The compounds in the Examples were found to be potent inhibitors of recombinant purified JAK2 kinase activity with an $IC_{50}$ of approximately 0.1 nM-20 μM.

JAK1 Enzyme Assay

For the JAK1 enzyme assay, reactions (50 uL) contained 5×IVGN buffer (50 mM Hepes, pH 7.5, 10 mM MgCl$_2$, 0.01% Brij-35, 1 mM EGTA, 0.1 mg/ml BSA), 2 mM DTT, 2.0 peptide substrate, 25 µM MgATP, 400 pM JAK1 enzyme and subject compound in 5% DMSO. Reactions were incubated for 60 mM at RT and quenched with 50 uL 2× quench detect buffer (10 mM EDTA, 25 mM HEPES, 0.1% TRITON X-100, 4.7 uM Europium-Py20 and 2.1 mg/mL streptavidin-APC). Incubate 1 hr at RT and read on a Victor V3 set to read Fluorescent Resonance Energy Transfer (Label 1: Lance 615, Label 2: Lance 665, For both: delay=50 us, window time=100 us, cycle=1000 us, flash energy level=103)

Peptide substrate is amino hexanoyl biotin-EQEDE-PEGDYFEWLE-NH2 (SEQ. ID.: 1) in DMSO.

Assay For JAK Family Protein Kinase Activity

Materials. Streptavidin•allophycocyanin conjugate (SA•APC) and Europium•cryptate (Eu•K) were from Packard Instrument Company. Eu•K conjugated pY20 was produced as described in Cummings, R. T.; McGovern, H. M.; Zheng, S.; Park, Y. W. and Hermes, J. D. Use Of A Phosphotyrosine-Antibody Pair As A General Detection Method In Homogeneous Time Resolved Fluorescence-Application To Human Immunodeficiency Viral Protease. *Analytical Biochemistry* 1999, 33, 79-93. Homogenous time resolved fluorescence (HTRF) measurements were made using the Discovery instrument from Packard. T-stim Culture Supplement was from Collaborative Biomedical Research. Recombinant mouse IL2 was from Pharmingen or R & D.

JAK family kinase expression. JAK3, TYK2 and JAK2 kinase domains with N-terminal "Flag" affinity tags were expressed in Sf9 cells using standard baculovirus methods. The human JAK3 gene was provided by Dr. John J. O'Shea (NIH). The human TYK2 gene was provided by Dr. Sandra Pellegrini (Insitut Pasteur). Human JAK2 kinase domain was cloned from a MOLT4 cDNA library (Clonetech).

Assay for JAK family protein kinase activity. Tyrosine kinase activity was measured by detection of the tyrosine phosphorylated peptide amino hexanoyl biotin-EQEDE-PEGDYFEWLE-NH$_2$ (SEQ. ID.: 1); (S, hereafter) detected by time-resolved fluorescence using a europium labeled antibody to phosphotyrosine (pY20). The JAK3(JH1) catalyzed phosphorylation reactions were carried out in a 30 uL total reaction volume. The compound was run at 5% DMSO and preincubated with enzyme buffer (EB). The EB comprised Invitrogen 5× kinase buffer (50 mM Hepes, pH 7.5, 10 mM MgCl$_2$, 0.01% Brij-35, 1 mM EGTA, 0.1 mg/ml BSA), 2 mM (final) DTT, 2 µM (final) S, and 250 pM (final) JAK3 enzyme. The assay was run at ATP K$_m$ (5 µM final) for 40 to 80 minutes. Reactions were run at ambient temperature and quenched with an equal volume of quench buffer (QB) (10 mM EDTA, 25 mM HEPES, 0.1% TRITON X-100) containing 50 µg/mL SA•APC conjugate and 0.75 nM Eu•K conjugated pY20. This mixture was incubated at ambient temperature for at least 60 minutes and read on an optimized fluorescent reader at Ex=320 nm and Em$_1$=665 nm (SA-APC) and Em$_2$=615 nM (Eu). The data was analyzed by using a standard 4P fit on the ratio of the Em results: (EM$_1$÷EM$_2$) *10,000.

The compounds in the Examples were found to be potent inhibitors of recombinant purified JAK3 kinase activity with an IC$_{50}$ of approximately 0.1 nM-20 µM.

In vitro PDK1 Kinase Assay

Activated recombinant full-length mT(Glu-Glu-Phe) tagged human PDK1 was used to determine whether the compounds of the instant invention modulate the enzymatic activity of this kinase.

The cDNA, encoding full-length PDK1, was subcloned into a baculovirus expression vector pBlueBac4.5 (Invitrogen), containing an in frame middle T tag (MEYMPME) (SEQ. ID.: 2) at its N-terminus. Soluble activated recombinant full-length mT(Glu-Glu-Phe) tagged human PDK1 was expressed in a baculovirus-infected Sf9 insect cells (Kemp Biotechnologies), according to the protocol recommended by the manufacturer. Immunoaffinity purification of the PDK1 kinase from the insect cell lysate was performed using a middle Tag antibody bound to Protein G-EE column. Upon elution using 50 mM Tris pH 7.4, 1 mM EDTA, 1 mM EGTA, 0.5 mM Na$_3$VO$_4$, 1 mM DTT, 50 mM NaF, Na Pyrophospate, Na-β-glycerophosphate, 10% glycerol, Complete, 1 µM microcystein, and 50 µg/ml EYMPME (SEQ. ID.: 3) peptide, fractions containing PDK1 protein were pooled together, based on SDS-PAGE and western blot analyses, and then analyzed for protein concentration using BCA Protein Assay (Pierce) with BSA as standard. The final product was aliqouted and flash frozen in liquid nitrogen before being stored at −80° C. Resulting PDK1 protein had MW of 64 kDa, was phosphorylated 'by default' and purified as an activated kinase from insect cells.

The procedure for determining the potency of a compound to inhibit PDK1 kinase comprises the following steps:

1. Prepare 3-fold serial diluted compound solutions in 100% dimethyl sulfoxide (DMSO) at 20× of the desired final concentrations in a 384-well plate.
2. Prepare a master reaction mix containing 62.5 mM HEPES (pH 7.5), 12.5 mM MgCl$_2$, 0.013% Brij-35, 1.25 mM EGTA, 2.5 mM dithiothreitol, 1.25 nM recombinant PDK1 and 375 nM biotinylated synthetic peptide substrate (Biotin-GGDGATMKTFCGGTPSDGDPDGGEFTEF-COOH) (SEQ. ID.: 4).
3. In a black assay plate, add 2.5 µl of compound solution (or DMSO) and 22.5 µl of master reaction mix per well. Pre-incubate for 10 min. Initiate the kinase reaction by adding 6 µl of 0.25 mM MgATP per well. Allow the reactions to proceed for 25 min at room temperature. The final conditions for the reaction are 1 nM PDK1, 300 nM peptide substrate, 5 µM MgATP, 10 mM MgCl$_2$, 2 mM DTT, 50 mM HEPES (pH 7.5), 0.01% Brij-35, 1 mM EGTA and 5% DMSO.
4. Stop the kinase reaction with 30 µl of Stop/Detection buffer containing 10 mM EDTA, 1× Lance Detection Buffer (cat. # CR97-100, PerkinElmer), 1% SuperBlocking in TBS (cat. # 37535, Pierce), 5 nM phospho-Akt(T308) monoclonal antibody (cat. # 4056, Cell Signaling Technologies), 5 nM Lance labeled Eu-Anti-rabbit IgG (cat. # AD0083, PerkinElmer), and 100 nM Streptavidin-allophycocyanin conjugate (cat. # PJ25S, Prozyme).

5. Read HTRF signals on an Envision reader (PerkinElmer) in HTRF mode after 60 min.
6. IC50 is determined by fitting the observed relationship between compound concentration and HTRF signal with a 4-parameter logistic equation.

The compounds in the Examples were found to be inhibitors of PDK1 kinase activity with an $IC_{50} \leq 100$ µM.

EXAMPLE 1

Compound 1-1

5-(1-methyl-1H-pyrazol-4-yl)-3-(6-piperazin-1-ylpyrazin-2-yl)-1H-pyrrolo[2,3-b]pyridine

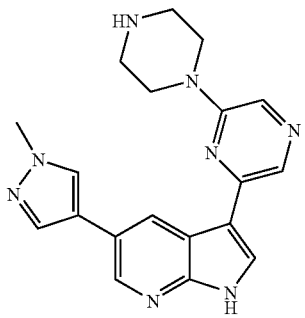

Step 1: 5-bromo-1-(phenylsulfonyl)-1H-pyrrolo[2,3-b]pyridine

To a stirred solution of 5-bromo-1H-pyrrolo[2,3-b]pyridine (20.0 g, 102 mmol) in DMF (400 ml) at 0° C. was added NaH (60% mineral oil dispersion; 4.87 g, 122 mmol) slowly (CAUTION: GAS EVOLUTION). The reaction mixture was stirred at 0° C. for 2 h. Benzenesulfonyl chloride (17.0 ml, 132 mmol) was added dropwise, and the reaction mixture was allowed to warm to ambient. After 1 hour the reaction mixture was cooled in an ice bath, and 100 mL of water was added slowly (CAUTION: GAS EVOLUTION, EXOTHERM). The reaction mixture was partitioned between ethyl acetate (500 mL) and brine (600 mL). The organic layer was washed with additional brine (500 mL), followed by saturated aqueous ammonium chloride (250 mL). The first and 3rd aqueous layers were combined and back-extracted with ethyl acetate (500 mL). The combined organics were dried over sodium sulfate, filtered and concentrated to a thick slurry. EtOAc (100 mL) was added, followed by hexanes (100 mL). The mixture was filtered, and the filter cake was rinsed with 1:1 EtOAc/Hexanes (50 mL) to afford 5-bromo-1-(phenylsulfonyl)-1H-pyrrolo[2,3-b]pyridine as a grey solid. The filtrate can be concentrated and purified by silica gel chromatography (EtOAc/Hexanes gradient) to afford additional product. LRMS (ESI) calculated for $C_{13}H_9BrN_2O_2S$ [M+H]$^+$, 337.0; found 336.9.

Step 2: 5-(1-methyl-1H-pyrazol-4-yl)-1-(phenylsulfonyl)-1H-pyrrolo[2,3-b]pyridine To a degassed (sparging with argon for 5 minutes), stirred solution of 1-methyl-4-(4,4,5,5-tetramethyl-1,3,2-dioxaborolan-2-yl)-1H-pyrazole (0.617 g, 2.97 mmol) and 5-bromo-1-(phenylsulfonyl)-1H-pyrrolo[2,3-b]pyridine (1.00 g, 2.97 mmol) in dioxane (12.0 ml) was added Pd(Ph$_3$P)$_4$ (0.171 g, 0.148 mmol), followed by a degassed aqueous solution of sodium carbonate (4.45 ml, 8.90 mmol). The reaction mixture was stirred under nitrogen at 100° C. for 2 h. The reaction mixture was cooled to room temperature and partitioned between EtOAc (25 mL) and saturated aqueous ammonium chloride (25 mL). The organic layer was dried over magnesium sulfate, filtered and concentrated to a crude residue. The residue was purified by silica gel chromatography (EtOAc/Hexanes gradient) to afford 5-(1-methyl-1H-pyrazol-4-yl)-1-(phenylsulfonyl)-1H-pyrrolo[2,3-b]pyridine as a white solid. LRMS (ESI) calculated for $C_{17}H_{14}N_4O_2S$ [M+H]$^+$, 339.1; found 339.1.

Step 3: 3-bromo-5-(1-methyl-1H-pyrazol-4-yl)-1-(phenylsulfonyl)-1H-pyrrolo[2,3-b]pyridine To a stirred solution of 5-(1-methyl-1H-pyrazol-4-yl)-1-(phenylsulfonyl)-1H-pyrrolo[2,3-b]pyridine (0.832 g, 2.46 mmol) in tetrahydrofuran (12.3 ml) was added N-bromosuccinimide (0.875 g, 4.92 mmol). The reaction mixture was stirred at room temperature for 16 hours. The reaction was quenched with 10% aqueous sodium thiosulfate solution (50 mL), then extracted with EtOAc (2×50 mL). The combined organic layers were dried over magnesium sulfate, filtered and concentrated. The crude residue was adsorbed on to silica gel and purified by silica gel chromatography (EtOAc/Hexanes gradient) to afford 3-bromo-5-(1-methyl-1H-pyrazol-4-yl)-1-(phenylsulfonyl)-1H-pyrrolo[2,3-b]pyridine as a white solid. LRMS (ESI) calculated for $C_{17}H_{13}BrN_4O_2S$ [M+H]$^+$, 417.0; found 417.0.

Step 4: 5-(1-methyl-1H-pyrazol-4-yl)-1-(phenylsulfonyl)-3-(4,4,5,5-tetramethyl-1,3,2-dioxaborolan-2-yl)-1H-pyrrolo[2,3-b]pyridine 3-bromo-5-(1-methyl-1H-pyrazol-4-yl)-1-(phenylsulfonyl)-1H-pyrrolo[2,3-b]pyridine (0.845 g, 2.03 mmol), potassium acetate (0.497 g, 5.06 mmol), tricyclohexylphosphine (0.0680 g, 0.243 mmol), bis(pinacolato)diboron (0.823 g, 3.24 mmol) and Pd$_2$(dba)$_3$ (0.0930 g, 0.101 mmol) were combined in dioxane (10 ml), sparged with argon for 5 minutes, and stirred at 100° C. for 16 h. The reaction mixture was cooled to room temperature, diluted with EtOAc (20 mL), and filtered through celite. The filtrate was concentrated to a crude residue that was carried on to the next step without further purification. LRMS calculated for $C_{23}H_{25}BN_4O_4S$ [M+H]$^+$, 465.2; found 465.1.

Step 5: Potassium 3-(trifluoroborate)-5-(1-methyl-1H-pyrazol-4-yl)-1-(phenylsulfonyl)-1H-pyrrolo[2,3-b]pyridine To a stirred solution of 5-(1-methyl-1H-pyrazol-4-yl)-1-(phenylsulfonyl)-3-(4,4,5,5-tetramethyl-1,3,2-dioxaborolan-2-yl)-1H-pyrrolo[2,3-b]pyridine (0.94 g, 2.024 mmol) (crude mixture from previous step) in acetone (7.2 ml) and water (2.9 ml) was added potassium hydrogen fluoride (0.158 g, 2.02 mmol). The reaction mixture was stirred at room temperature for 1 hour. The reaction mixture was concentrated to a crude solid (concentrated to dryness several using acetone to drive off water) that was then triturated in hot (ca. 55° C.) acetone. The mixture was filtered and the filtrate concentrated to a final volume of approximately 10 mL. Diethyl ether (10 mL) was added dropwise to promote crystallization. The resulting suspension was cooled in an ice bath for 15 minutes, then filtered, rinsing the filter cake with diethyl ether to afford potassium 3-(trifluoroborate)-5-(1-methyl-1H-pyrazol-4-yl)-1-(phenylsulfonyl)-1H-pyrrolo[2,3-b]pyridine as a grey solid. $^1$H NMR (600 MHz, DMSO-D$_6$) δ 8.42 (d, 1H); 8.13 (s, 1H); 8.00 (dd, 2H); 7.91 (d, 1H); 7.80 (d, 1H); 7.62 (t, 1H); 7.54 (t, 2H); 7.20 (s, 1H); 3.82 (s, 3H).

Step 6: tert-butyl 4-(6-chloropyrazin-2-yl)piperazine-1-carboxylate 2,6-dichloropyrazine (10.0 g, 67.1 mmol), tert-butyl piperazine-1-carboxylate (12.5 g, 67.1 mmol) and cesium carbonate (43.7 g, 134 mmol) were added to a round bottom flask and flushed with nitrogen. DMF (300 ml) was then added and the reaction was stirred at 100° C. for 3 hours. The reaction mixture was cooled to room temperature, then diluted with EtOAc (600 mL) and washed with brine (600 mL). The aqueous layer was washed with additional EtOAc (600 mL). The combined organic layers were dried over sodium sulfate, filtered and concentrated to a crude residue that was purified by silica gel chromatography to afford tert-butyl 4-(6-chloropyrazin-2-yl)piperazine-1-carboxylate as an off-white solid. LRMS calculated for $C_{13}H_{19}ClN_4O_2[M^+H]^+$, 299.1; found 299.1.

Step 7: tert-butyl 4-{6-[5-(1-methyl-1H-pyrazol-4-yl)-1-(phenylsulfonyl)-1H-pyrrolo[2,3-b]pyridin-3-yl]pyrazin-2-yl}piperazine-1-carboxylate tert-butyl 4-(6-chloropyrazin-2-yl)piperazine-1-carboxylate (0.050 g, 0.17 mmol), potassium 3-(trifluoroborate)-5-(1-methyl-1H-pyrazol-4-yl)-1-(phenylsulfonyl)-1H-pyrrolo[2,3-b]pyridine (0.074 g, 0.17 mmol), PdCl$_2$(dppf)-CH$_2$Cl$_2$ adduct (6.8 mg, 8.4 ml) and TEA (0.047 ml, 0.34 mmol) were combined in nPrOH (0.84 ml) and sparged with argon for 5 minutes. The reaction mixture was stirred under nitrogen at 97° C. for 1 h. The reaction mixture was cooled to room temperature, and diluted with EtOAc (10 mL). Silica gel was added, and concentrated to a crude residue that was purified by silica gel chromatography (EtOAc/Hexanes gradient) to afford tert-butyl 4-{6-[5-(1-methyl-1H-pyrazol-4-yl)-1-(phenylsulfonyl)-1H-pyrrolo[2,3-b]pyridin-3-yl]pyrazin-2-yl}piperazine-1-carboxylate as a pale yellow solid. LRMS calculated for $C_{30}H_{32}N_8O_4S$ [M+H]$^+$, 601.2; found 601.2.

Step 8: tert-butyl 4-{6-[5-(1-methyl-1H-pyrazol-4-yl)-1H-pyrrolo[2,3-b]pyridin-3-yl]pyrazin-2-yl}piperazine-1-carboxylate To a stirred solution of tert-butyl 4-{6-[5-(1-methyl-1H-pyrazol-4-yl)-1-(phenylsulfonyl)-1H-pyrrolo[2,3-b]pyridin-3-yl]pyrazin-2-yl}piperazine-1-carboxylate (0.077 g, 0.13 mmol) in MeOH (1.3 ml) was added potassium carbonate (0.053 g, 0.34 mmol). The reaction mixture was stirred at 50° C. for 1 hour, then at room temperature for 16 hours. The reaction mixture was diluted with MeOH (10 mL) and DCM (10 mL), silica gel was added, and concentrated to a crude residue. The crude residue was purified by silica gel chromatography (EtOAc/Hexanes gradient, followed by MeOH/DCM gradient) to afford tert-butyl 4-{6-[5-(1-methyl-1H-pyrazol-4-yl)-1H-pyrrolo[2,3-b]pyridin-3-yl]pyrazin-2-yl}piperazine-1-carboxylate as a white solid. LRMS calculated for $C_{24}H_{28}N_8O_2$ [M+H]$_+$, 461.2; found 461.2.

Step 9: 5-(1-methyl-1H-pyrazol-4-yl)-3-(6-piperazin-1-ylpyrazin-2-yl)-1H-pyrrolo[2,3-b]pyridine (hydrochloride salt)

tert-butyl 4-{6-[5-(1-methyl-1H-pyrazol-4-yl)-1H-pyrrolo[2,3-b]pyridin-3-yl]pyrazin-2-yl}piperazine-1-carboxylate (0.047 g, 0.10 mmol) was suspended in dioxane (1.0 ml). 4M HCl in dioxane (1.0 ml) was added, and the reaction mixture was stirred at room temperature for 45 min. The reaction mixture was filtered to afford 5-(1-methyl-1H-pyrazol-4-yl)-3-(6-piperazin-1-ylpyrazin-2-yl)-1H-pyrrolo[2,3-b]pyridine as an orange/yellow solid (hydrochloride salt). $^1$H NMR (600 MHz, DMSO-D$_6$) δ 12.4 (br s, 1H); 9.41 (br s, 2H); 8.71 (br d, 1H); 8.56 (s, 1H); 8.55 (d, 1H); 8.39 (d, 1H); 8.19 (s, 1H); 8.18 (s, 1H); 7.89 (s, 1H); 3.93 (br t, 4H); 3.87 (s, 3H); 3.25 (br m, 4H). LRMS calculated for $C_{19}H_{20}N_8$ [M+H]$^+$, 361.2; found 361.2.

The compounds listed below in Table 1 were prepared in analogy to the preparation of Compound 1-1 starting from potassium 3-(trifluoroborate)-5-(1-methyl-1H-pyrazol-4-yl)-1-(phenylsulfonyl)-1H-pyrrolo[2,3-b]pyridine, and utilizing the appropriate substituted-6-chloropyrazine in the requisite Suzuki coupling described above. Unless otherwise indicated, the compounds were isolated as their hydrochloride salts.

TABLE 1

| Compound | Structure | Name | [M + H] + calc | [M + H] + obs |
|---|---|---|---|---|
| 1-2 | 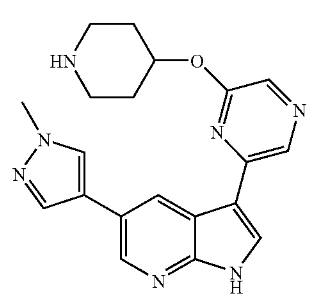 | 5-(1-methyl-1H-pyrazol-4-yl)-3-[6-(piperidin-4-yloxy)pyrazin-2-yl]-1H-pyrrolo[2,3-b]pyridine | 376.2 | 376.2 |

TABLE 1-continued

| Compound | Structure | Name | [M + H] + calc | [M + H] + obs |
|---|---|---|---|---|
| 1-3 | (free base) | 3-[6-(cyclohexyloxy)pyrazin-2-yl]-5-(1-methyl-1H-pyrazol-4-yl)-1H-pyrrolo[2,3-b]pyridine | 375.2 | 375.2 |
| 1-4 | 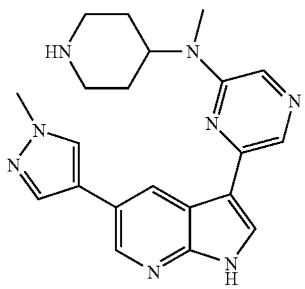 | N-methyl-6-[5-(1-methyl-1H-pyrazol-4-yl)-1H-pyrrolo[2,3-b]pyridin-3-yl]-N-piperidin-4-ylpyrazin-2-amine | 389.2 | 389.2 |

Compound 1-2 was prepared using tert-butyl 4-[(6-chloropyrazin-2-yl)oxy]piperidine-1-carboxylate in the requisite suzuki coupling step:

tert-butyl 4-[(6-chloropyrazin-2-yl)oxy]piperidine-1-carboxylate

To a stirred solution of tert-butyl 4-hydroxypiperidine-1-carboxylate (3.80 g, 18.9 mmol) in DMF (76 ml) was added sodium hydride (60% mineral oil dispersion; 0.906 g, 22.7 mmol) at 0° C. The reaction mixture was stirred for 1 hour, until hydrogen evolution ceased. 2,6 dichloropyrazine (2.81 g, 18.9 mmol) was added, and the reaction mixture was allowed to warm to room temperature. After 1 hour, the reaction was quenched with brine (100 mL) and extracted with EtOAc (2×200 mL). The combined EtOAc layers were dried over magnesium sulfate, filtered and concentrated to a crude residue that was purified by silica gel chromatography (EtOAc/Hexanes gradient) to afford tert-butyl 4-[(6-chloropyrazin-2-yl)oxy]piperidine-1-carboxylate as a yellow solid. LRMS calculated for $C_{14}H_{20}ClN_3O_3$ [M+Na]$^+$, 336.1; found 336.1.

Compound 1-3 was prepared using 2-chloro-6-(cyclohexyloxy)pyrazine (prepared in analogy to the procedure described above). LRMS calculated for $C_{10}H_{13}ClN_2O$ [M+H]$^+$, 213.1; found 213.1.

Compound 1-4 was prepared using tert-butyl 4-[(6-chloropyrazin-2-yl)(methyl)amino]piperidine-1-carboxylate (procedure below).

Step 1: tert-butyl 4-[(6-chloropyrazin-2-yl)amino]piperidine-1-carboxylate tert-butyl 4-[(6-chloropyrazin-2-yl)amino]piperidine-1-carboxylate was prepared from 2,6-dichloropyrazine and tert-butyl 4-aminopiperidine-1-carboxylate using the conditions described for the preparation of tert-butyl 4-(6-chloropyrazin-2-yl)piperazine-1-carboxylate (Compound 1, Step 6). LRMS calculated for $C_{14}H_{21}ClN_4O_2$ [M+Na]+, 335.1; found 335.1.

Step 2: tert-butyl 4-[(6-chloropyrazin-2-yl)(methyl)amino]piperidine-1-carboxylate To a stirred solution of tert-butyl 4-[(6-chloropyrazin-2-yl)amino]piperidine-1-carboxylate (0.165 g, 0.528 mmol) in THF (2.6 ml) was added methyl iodide (0.165 ml, 2.64 mmol). The solution was cooled to 0° C., and a solution of NaHMDS in THF (1M; 1.06 ml, 1.06 mmol) was added. The reaction mixture was allowed to warm to room temperature and stirred for 2 h. The reaction was quenched with saturated aqueous ammonium chloride (50 mL, and extracted with EtOAc (2×50 mL). The combined EtOAc layers were washed with brine (50 mL), dried over magnesium sulfate, filtered and concentrated. The crude residue was purified by silica gel chromatography (EtOAc/Hexanes gradient) to afford tert-butyl 4-[(6-chloropyrazin-2-yl)(methyl)amino]piperidine-1-carboxylate as a yellow oil. LRMS calculated for $C_{15}H_{23}ClN_4O_2$ [M+Na]$^+$, 349.2; found 349.0.

EXAMPLE 2

Compound 2-1

3-[6-(piperidin-4-yloxy)pyrazin-2-yl]-5-(1H-pyrazol-4-yl)-1H-pyrrolo[2,3-b]pyridine

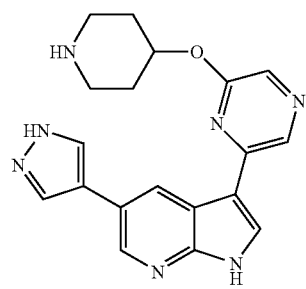

Step 1: 1-(phenylsulfonyl)-5-(1H-pyrazol-4-yl)-1H-pyrrolo[2,3-b]pyridine

To a degassed (sparging with argon for 5 minutes), stirred solution of 4-(4,4,5,5-tetramethyl-1,3,2-dioxaborolan-2yl)-pyrazole-1-carboxylic acid tert-butyl ester (1.31 g, 4.45 mmol) and 5-bromo-1-(phenylsulfonyl)-1H-pyrrolo[2,3-b]pyridine (1.00 g, 2.97 mmol) in dioxane (12.0 ml) was added $Pd(Ph_3P)_4$ (0.171 g, 0.148 mmol), followed by a degassed aqueous solution of sodium carbonate (4.45 ml, 8.90 mmol). The reaction mixture was stirred under nitrogen at 100° C. for 1 hour. The reaction mixture was cooled to room temperature and partitioned between EtOAc (50 mL) and saturated aqueous ammonium chloride (50 mL). The organic layer was dried over magnesium sulfate, filtered and concentrated to a crude residue. The residue was purified by silica gel chromatography (EtOAc/Hexanes gradient) to afford 1-(phenylsulfonyl)-5-(1H-pyrazol-4-yl)-1H-pyrrolo[2,3-b]pyridine as a yellow solid. LRMS (ESI) calculated for $C_{16}H_{12}N_4O_2S$ $[M+H]^+$, 325.1; found 325.0.

Step 2: tert-butyl 4-[1-(phenylsulfonyl)-1H-pyrrolo[2,3-b]pyridine-5-yl]-1H-pyrazole-1-carboxylate To a stirred solution of 1-(phenylsulfonyl)-5-(1H-pyrazol-4-yl)-1H-pyrrolo[2,3-b]pyridine (0.588 g, 1.81 mmol) in dichloromethane (9 mL) was added di-tert-butyl dicarbonate (0.396 g, 1.81 mmol), triethylamine (0.51 mL, 3.63 mmol), and 4-dimethylaminopyridine (0.221 g, 1.81 mmol). The reaction was stirred at room temperature for 1 h. The reaction mixture was diluted with dichloromethane (50 mL) and washed with 10% aqueous citric acid (50 mL). The organic layer was dried over magnesium sulfate, filtered and concentrated. The crude residue was purified by silica gel chromatography (EtOAc/Hexanes gradient) to afford tert-butyl 4-[1-(phenylsulfonyl)-1H-pyrrolo[2,3-b]pyridine-5-yl]-1H-pyrazole-1-carboxylate as a white solid. LRMS (ESI) calculated for $C_{21}H_{20}N_4O_2S$ $[M+H]^+$, 425.1; found 425.0.

Tert-butyl 4-[1-(phenylsulfonyl)-3-(4,4,5,5-tetramethyl-1,3,2-dioxaborolan-2-yl)-1H-pyrrolo[2,3-b]pyridine-5-yl]-1H-pyrazole-1-carboxylate was prepared by the method shown in Scheme 1, omitting step 5. The crude residue was purified by column chromatography (EtOAc/hexanes gradient) to afford tert-butyl 4-[1-(phenylsulfonyl)-3-(4,4,5,5-tetramethyl-1,3,2-dioxaborolan-2-yl)-1H-pyrrolo[2,3-b]pyridine-5-yl]-1H-pyrazole-1-carboxylate as a yellow oil. LRMS (ESI) calculated for $C_{27}H_{31}BN_4O_6S$ $[M+H]^+$, 551.2; found 551.2.

Step 3: tert-butyl 4-[(6-chloropyrazin-2-yl)oxy]piperidine-1-carboxylate

To a stirred solution of 1-boc-4-hydroxypiperidine (3.80 g, 18.9 mmol) in DMF (76 mL) at 0° C. was added sodium hydride (60% mineral oil dispersion; 0.906 g, 22.7 mmol). Once hydrogen evolution had ceased, 2,6-dichloropyrazine (2.81 g, 18.9 mmol) was added and the reaction mixture was allowed to warm to ambient temperature. After 1 h, the reaction mixture was quenched with brine (100 mL) and extracted with EtOAc (2×100 mL). The combined organics were dried over magnesium sulfate, filtered and concentrated. The crude residue was purified by silica gel chromatography (EtOAc/Hexanes gradient) to afford tert-butyl 4-[(6-chloropyrazin-2-yl)oxy]piperidine-1-carboxylate as a yellow solid. LRMS (ESI) calculated for $C_{14}H_{20}ClN_3O_3$ 336.1; found $[M+Na]^+$, 336.1.

Step 4: tert-butyl 4-([{6[1-(phenylsulfonyl)-5-(1H-pyrazol-4-yl)-1H-pyrrolo[2,3-b]pyridine-3-yl]pyrazin-2-yl}oxy)cyclohexanecarboylate To a degassed (sparging with argon for 5 minutes), stirred solution of tert-butyl 4-[1-(phenylsulfonyl)-3-(4,4,5,5-tetramethyl-1,3,2-dioxaborolan-2-yl)-1H-pyrrolo[2,3-b]pyridine-5-yl]-1H-pyrazole-1-carboxylate (0.10 g, 0.18 mmol) and tert-butyl 4-[(6-chloropyrazin-2-yl)oxy]piperidine-1-carboxylate (0.057 g, 0.18 mmol) was added $Pd(Ph_3P)_4$ (10.5 mg, 9.1 μmol), followed by a degassed aqueous solution of sodium carbonate (0.273 ml, 0.550 mmol). The reaction mixture was stirred under nitrogen at 100° C. for 16 hours. The reaction mixture was cooled to room temperature and partitioned between EtOAc (25 mL) and saturated aqueous ammonium chloride (25 mL). The organic layer was dried over magnesium sulfate, filtered and concentrated to a crude residue. The residue was purified by silica gel chromatography (EtOAc/Hexanes gradient) to afford tert-butyl 4-({6[1-(phenylsulfonyl)-5-(1H-pyrazol-4-yl)-1H-pyrrolo[2,3-b]pyridine-3-yl]pyrazin-2-yl}oxy)cyclohexanecarboylate as a white solid. LRMS (ESI) calculated for $C_{30}H_{31}N_7O_5S$ $[M+H]^+$, 602.2; found 602.0.

3-[6-(piperdin-4-yloxy)pyrazin-2-yl]-5-(1H-pyrazol-4-yl)-1H-pyrrolo[2,3-b]pyridine was prepared by the method shown in Example 1. $^1$H NMR (600 MHz, DMSO-$D_6$) δ 12.52 (br s, 1H); 9.22 (br s, 1H); 9.03 (br s, 1H); 8.83 (s, 1H); 8.78 (s, 1H); 8.63 (s, 1H); 8.43 (d, 1H); 8.25 (s, 2H); 8.06 (s, 1H); 5.48 (m, 1H); 3.21 (br m, 2H); 3.09 (br m, 2H); 2.23 (m, 2H); 2.05 (m, 2H). LRMS (ESI) calculated for $C_{19}H_{19}N_7O$ $[M+H]^+$, 362.2; found 362.0.

The compounds listed below in Table 2 were prepared in analogy to the preparation of Compound 2-1 starting from tert-butyl 4-[1-(phenylsulfonyl)-3-(4,4,5,5-tetramethyl-1,3,2-dioxaborolan-2-yl)-1H-pyrrolo[2,3-b]pyridine-5-yl]-1H-pyrazole-1-carboxylate, and utilizing the appropriate substituted-6-chloropyrazine in the requisite Suzuki coupling described above. Unless otherwise indicated, the compounds were isolated as their hydrochloride salts.

TABLE 2

| Compound | Structure | Name | [M + H] + calc | [M + H] + obs |
|---|---|---|---|---|
| 2-2 | 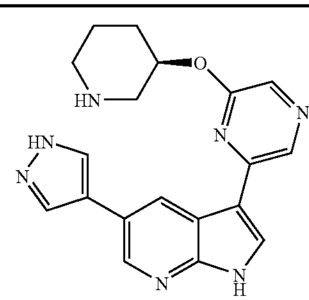 | 3-{6-[(3R)-piperdin-3-yloxy]pyrazin-2-yl}-5-(1H-pyrazol-4-yl)-1H-pyrrolo[2,3-b]pyridine | 362.2 | 362.1 |

TABLE 2-continued

| Compound | Structure | Name | [M + H]+ calc | [M + H]+ obs |
|---|---|---|---|---|
| 2-3 | 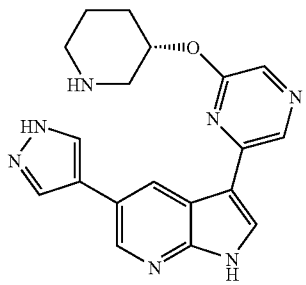 | 3-{6-[(3S)-piperdin-3-yloxy]pyrazin-2-yl}-5-(1H-pyrazol-4-yl)-1H-pyrrolo[2,3-b]pyridine | 362.2 | 362.1 |
| 2-4 | 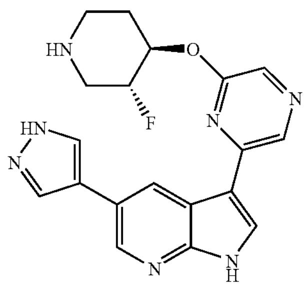 | trans-3-{6-[(3-fluoropiperdin-4-yl)oxy]pyrazin-2-yl}-5-(1H-pyrazol-4-yl)-1H-pyrrolo[2,3-b]pyridine | 380.2 | 380.1 |
| 2-5 | 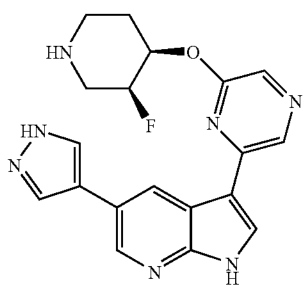 | cis-3-{6-[(3-fluoropiperdin-4-yl)oxy]pyrazin-2-yl}-5-(1H-pyrazol-4-yl)-1H-pyrrolo[2,3-b]pyridine | 380.2 | 380.1 |
| 2-6 | 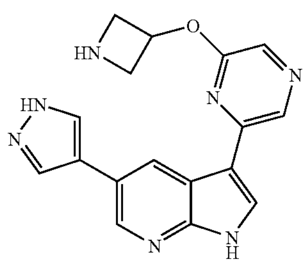 | 3-[6-(azetidine-3-yloxy)pyrazin-2-yl]-5-(1H-pyrazol-4-yl)-1H-pyrrolo[2,3-b]pyridine | 334.1 | 334.1 |
| 2-7 | 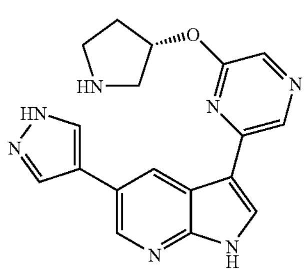 | 5-(1H-pyrazol-4-yl)-3-{6-[(3S)-pyrrolidin-3-yloxy]pyrazin-2-yl-1H-pyrrolo[2,3-b]pyridine | 348.2 | 348.1 |

TABLE 2-continued

| Compound | Structure | Name | [M + H]+ calc | [M + H]+ obs |
|---|---|---|---|---|
| 2-8 | 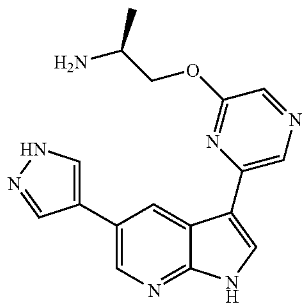 | (2S)-1-({6-[5-(1H-pyrazol-4-yl)-1H-pyrrolo[2,3-b]pyridin-3-yl]pyrazin-2-yl}oxy)propan-2-amine | 336.2 | 336.1 |
| 2-9 | 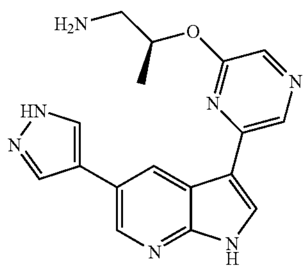 | (2S)-2-({6-[5-(1H-pyrazol-4-yl)-1H-pyrrolo[2,3-b]pyridin-3-yl]pyrazin-2-yl}oxy)propan-1-amine | 336.2 | 336.1 |
| 2-10 | 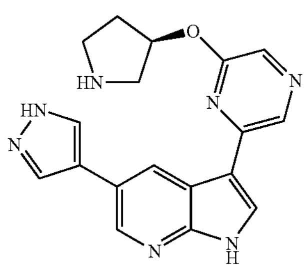 | 5-(1H-pyrazol-4-yl)-3-{6-[(3R)-pyrrolidin-3-yloxy]pyrazin-2-yl-1H-pyrrolo[2,3-b]pyridine | 348.2 | 348.1 |
| 2-11 | 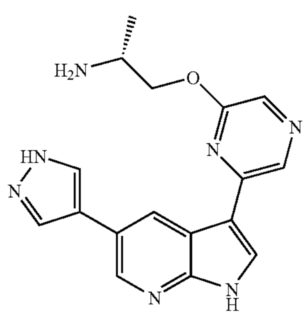 | (2R)-1-({6-[5-(1H-pyrazol-4-yl)-1H-pyrrolo[2,3-b]pyridin-3-yl]pyrazin-2-yl}oxy)propan-2-amine | 336.2 | 336.1 |
| 2-12 | 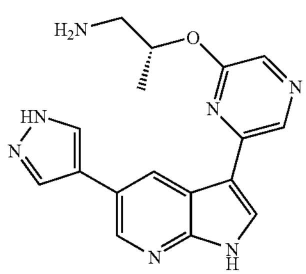 | (2R)-2-({6-[5-(1H-pyrazol-4-yl)-1H-pyrrolo[2,3-b]pyridin-3-yl]pyrazin-2-yl}oxy)propan-1-amine | 336.2 | 336.1 |

Compound 2-2 was prepared using tert-butyl (3R)-3-[(6-chloropyrazin-2-yl)oxy]piperidine-1-carboxylate (prepared in analogy to the procedure described for Compound 2-1). LRMS (ESI) calculated for $C_{14}H_{20}ClN_3O_3$ [M+Na]+, 336.1; found 336.0.

Compound 2-3 was prepared using tert-butyl (3S)-3-[(6-chloropyrazin-2-yl)oxy]piperidine-1-carboxylate (prepared in analogy to the procedure described for Compound 2-1). LRMS (ESI) calculated for $C_{14}H_{20}ClN_3O_3$ [M+Na]+, 336.1; found 336.0.

Compound 2-4 was prepared using tert-butyl trans-4-[(6-chloropyrazin-2-yl)oxy]-3-fluoropiperidine-1-carboxylate in the requisite Suzuki coupling step:

Step 1: piperidin-4-one hydrochloride

To a solution of 1-boc-4-piperidone (2300 g, 11.56 mol) in dioxane was added a solution of HCl (g)/dioxane (4 L, 10 mol/L) slowly at 0° C. After the addition, the reaction mixture was stirred for 4 hours and TLC (EtOAc/petroleum ether=1:5) showed the reaction was complete. The solvent was removed to afford piperidin-4-one hydrochloride as a brown solid.

Step 2: benzyl 4-oxopiperidine-1-carboxylate

To a stirred solution of piperidin-4-one hydrochloride (1567 g, 11.56 mol) and triethylamine (1400 g, 13.87 mol) in dichloromethane (12 L) was added benzyl chloroformate (1965 g, 11.55 mol) dropwise at 0° C. After the addition, the reaction mixture was allowed to warm to room temperature and stirred overnight. TLC (EtOAc/petroleum ether=1:5) showed the reaction was complete. The mixture was washed with water (3 L) and brine (1 L), dried over sodium sulfate and concentrated to afford benzyl 4-oxopiperidine-1-carboxylate as a colorless oil.

Step 3: benzyl 4-[(trimethylsilyl)oxy]-3,6-dihydropyridine-1(2H)-carboxylate To a stirred solution of benzyl 4-oxopiperidine-1-carboxylate (300 g, 1.29 mol) and TMSCl (280 g, 2.58 mol) in DMF (1600 mL) was added triethylamine (457 g, 4.52 mol) at room temperature. After the addition, the reaction mixture was slowly heated to 85° C. and stirred overnight. TLC (EtOAc/Petroleum ether=1:10) showed that the starting material was consumed completely. The reaction mixture was poured into aqueous $NaHCO_3$ (5% w/v) at 0° C. with vigorous stirring and extracted with petroleum ether (3 L, 1 L). The organic layer was dried over sodium sulfate and concentrated to afford benzyl 4-[(trimethylsilyl)oxy]-3,6-dihydropyridine-1(2 H)-carboxylate as a brown oil. $^1$H NMR (600 MHz, $CDCl_3$-$D_6$) δ 7.40-7.30 (m, 5H); 5.13 (s, 2H); 4.80 (d, 1H); 3.95 (s, 2H); 3.60 (s, 2H); 2.10 (s, 2H); 0.20 (s, 9H).

Step 4: benzyl 3-fluoro-4-oxopiperidine-1-carboxylate

To a solution of benzyl 4-[(trimethylsilyl)oxy]-3,6-dihydropyridine-1(2H)-carboxylate (800 g, 2.61 mol) in acetonitrile was added Selectfluor™ (932.8 g, 2.63 mol) in small portions under nitrogen at 0° C. After the addition was complete, the reaction mixture was allowed to warm to room temperature and stirred overnight. TLC (EtOAc/petroleum ether=1:1) indicated the reaction was complete, and the solvent was removed in vacuo. The residue was triturated with ethyl acetate (5 L, 3 L) for 30 min and filtered. The filtrate was concentrated and the syrup was purified by column chromatography (EtOAc/petroleum ether=1:10 to 2:3) to afford benzyl 3-fluoro-4-oxopiperidine-1-carboxylate. $^1$H NMR (600 MHz, $CDCl_3$-$D_6$) 7.40-7.30 (m, 5H); 5.20 (s, 2H); 5.00-4.70 (d, 1H); 5.20-4.90 (d, 1H); 4.30-4.20 (m, 1H); 3.40-3.20 (m, 2H); 2.50 (s, 2H).

Step 5: benzyl cis-3-fluoro-4-hydroxypiperidine-1-carboxylate

To a solution of benzyl 3-fluoro-4-oxopiperidine-1-carboxylate (200 g, 0.797 mol) in methanol (1 L) was added $NaBH_4$ (24.4 g, 0.636 mol) in portions at 0° C. After the addition, the mixture was stirred for 4 h and then quenched with water (200 mL). The mixture was concentrated, and then ethyl acetate and water were added to the residue. The organic layer was separated, dried over sodium sulfate and concentrated. The residue was purified via column chromatography (EtOAc/petroleum ether=1:6) to afford benzyl cis-3-fluoro-4-hydroxypiperidine-1-carboxylate and benzyl trans-3-fluoro-4-hydroxypiperidine-1-carboxylate. $^1$H NMR (600 MHz, $CDCl_3$-$D_6$) δ 7.50-7.30 (m, 5H); 5.13 (s, 2H); 4.70-4.50 (d, 1H); 4.10-3.70 (m, 3H); 3.48 (s, 1H); 3.23 (s, 1H); 2.50 (s, 1H); 1.90-1.70 (m, 2H).

Step 6: benzyl trans-3-fluoro-4-[(4-nitrobenzyl)oxy]piperidine-1-carboxylate To a solution of triphenylphosphine (120.1 g, 0.458 mol) in THF (2 L) was added DIAD (92.6 g, 0.458 mol) with stirring under nitrogen at 0° C. The resulting suspension was stirred for 40 min, and then a solution of benzyl cis-3-fluoro-4-hydroxypiperidine-1-carboxylate (58 g, 0.229 mol) and 4-nitrobenzoic acid (45.9 g, 0.275 mol) in THF was added slowly over 1.5 h. The resulting orange solution was allowed to warm to room temperature and stirred for 48 h. The mixture was concentrated under reduced pressure to a crude oil was purified by column chromatography (EtOAc:petroleum ether=1:40) to afford benzyl trans-3-fluoro-4-[(4-nitrobenzyl)oxy]piperidine-1-carboxylate as an off-white solid.

Step 7: benzyl trans-3-fluoro-4-hydroxypiperidine-1-carboxylate

To a solution of benzyl trans-3-fluoro-4-[(4-nitrobenzyl)oxy]piperidine-1-carboxylate (180 g, 0.45 mol) in THF/$H_2O$ (1500 mL) was added LiOH (39 g, 0.9 mol) in portions at 0° C. After the addition, the reaction mixture was allowed to warm to room temperature and stirred overnight. TLC (EtOAc:petroleum ether=1:2) showed the starting material was consumed completely. The reaction mixture was extracted with EtOAc (3×500 mL). The combined organic layers were washed with brine (800 mL), dried over anhydrous $Na_2SO_4$ and concentrated to a crude residue. The residue was purified by column chromatography (EtOAc:petroleum ether=1:20) to afford benzyl trans-3-fluoro-4-hydroxypiperidine-1-carboxylate as a white solid.

Step 8: tert-butyl trans-3-fluoro-4-hydroxypiperidine-1-carboxylate benzyl trans-3-fluoro-4-hydroxypiperidine-1-carboxylate (56.9 g, 0.225 mol) was hydrogenated in the presence of Pd(OH)$_2$/C and Boc$_2$O (51.43 g, 0.236 mol) under 35 psi of hydrogen at room temperature in methanol. The reaction was monitored by TLC (EtOAc/petroleum ether=1:2). Upon completion, the reaction mixture was filtered and the filtrate was concentrated in vacuum to give a white solid that was re-crystallized from petroleum ether/methanol to afford tert-butyl trans-3-fluoro-4-hydroxypiperidine-1-carboxylate. LRMS (ESI) calculated for $C_{10}H_{18}FNO_3$ [M+H]$^+$, 220.1; found 219.7.

Step 9: tert-butyl trans-4-[(6-chloropyrazin-2-yl)oxy]-3-fluoropiperidine-1-carboxylate tert-butyl trans-4-[(6-chloropyrazin-2-yl)oxy]-3-fluoropiperidine-1-carboxylate was prepared from 2,6-dichloropyrazine and tert-butyl trans-3-fluoro-4-hydroxypiperidine-1- carboxylate using the conditions described for the preparation of tert-butyl 4-[(6-chloropyrazin-2-yl)oxy]piperidine-1-carboxylate (Compound 1, Step 3). LRMS (ESI) calculated for $C_{14}H_{19}ClFN_3O_3[M+Na]^+$, 354.1; found 354.1.

Compound 2-5 was prepared using tert-butyl cis-4-[(6-chloropyrazin-2-yl)oxy]-3-fluoropiperidine-1-carboxylate in the requisite Suzuki coupling step:

Step 1; tert-butyl cis-3-fluoro-4-hydroxypiperidine-1-carboxylate tert-butyl cis-3-fluoro-4-hydroxypiperidine-1-carboxylate was prepared in analogy to tert-butyl trans-3-fluoro-4-hydroxypiperidine-1-carboxylate as described for Compound 2-4. LRMS (ESI) calculated for $C_{10}H_{18}FNO_3$ $[M+H]^+$, 220.1; found 219.7.

Step 2: tert-butyl cis-4-[(6-chloropyrazin-2-yl)oxy]-3-fluoropiperidine-1-carboxylate tert-butyl cis-4-[(6-chloropyrazin-2-yl)oxy]-3-fluoropiperidine-1-carboxylate was prepared from 2,6-dichloropyrazine and tert-butyl cis-3-fluoro-4-hydroxypiperidine-1-carboxylate using the conditions described for the preparation of tert-butyl 4-[(6-chloropyrazin-2-yl)oxy]piperidine-1-carboxylate (Compound 1, Step 3). LRMS (ESI) calculated for $C_{14}H_{19}ClFN_3O_3[M+Na]^+$, 354.1; found 354.1.

Compound 2-6 was prepared using tert-butyl 3-[(6-chloropyrazin-2-yl)oxy]azetidine-1-carboxylate (prepared in analogy to the procedure described for Compound 2-1). LRMS (ESI) calculated for $C_{12}H_{16}ClN_3O_3$ $[M+Na]^+$, 308.1; found 308.0.

Compound 2-7 was prepared using tert-butyl (3S)-3-[(6-chloropyrazin-2-yl)oxy]pyrrolidine-1-carboxylate (prepared in analogy to the procedure described for Compound 2-1). LRMS (ESI) calculated for $C_{13}H_{18}ClN_3O_3$ $[M+Na]^+$, 322.1; found 322.0.

Compound 2-8 was prepared using tert-butyl {(1S)-2-[(6-chloropyrazin-2-yl)oxy]-1-methylethyl}carbamate in the requisite Suzuki coupling step:

tert-butyl {(1S)-2-[(6-chloropyrazin-2-yl)oxy]-1-methylethyl}carbamate

Synthesis Adapted from the Following Reference
Shafir, A.; Lichtor, P. A.; Buchwald, S. L. *J. Am. Chem. Soc.* 2007, 129, 3490-3491.

To a degassed stirred solution of boc-L-alaminol (0.12 g, 0.67 mmol) and 2,6-dichloropyrazine (0.10 g, 0.67 mmol) in toluene (3.5 mL) was added 3,4,7,8-tetramethyl-1,10-phenanthroline (1.6 mg, 6.7 μmol), copper iodide (6.4 mg, 0.034 mmol) and cesium carbonate (0.44 g, 1.3 mmol). The reaction mixture was stirred under nitrogen for 16 hours. The reaction mixture was cooled to room temperature, diluted with EtOAc (10 mL), and filtered through celite. The filtrate was concentrated to a crude residue. The residue was purified by silica gel chromatography (EtOAc/Hexanes gradient) to afford tert-butyl {(1S)-2-[(6-chloropyrazin-2-yl)oxy]-1-methylethyl}carbamate as a white solid. LRMS (ESI) calculated for $C_{12}H_{18}ClN_3O_3[M+Na]^+$, 310.1; found 310.0.

Compound 2-9 was prepared using tert-butyl {(2S)-2-[(6-chloropyrazin-2-yl)oxy]propyl}carbamate (prepared in analogy to the procedure described for Compound 2-8). LRMS (ESI) calculated for $C_{12}H_{18}ClN_3O_3$ $[M+Na]^+$, 310.1; found 310.0.

Compound 2-10 was prepared using tert-butyl (3R)-3-[(6-chloropyrazin-2-yl)oxy]pyrrolidine-1-carboxylate (prepared in analogy to the procedure described for Compound 2-1). LRMS (ESI) calculated for $C_{13}H_{18}ClN_3O_3$ $[M+Na]^+$, 322.1; found 322.0.

Compound 2-11 was prepared using tert-butyl {(1R)-2-[(6-chloropyrazin-2-yl)oxy]-1-methylethyl}carbamate (prepared in analogy to the procedure described for compound 2-8). LRMS (ESI) calculated for $C_{12}H_{18}ClN_3O_3[M+Na]^+$, 310.1; found 310.0.

Compound 2-12 was prepared using tert-butyl {(2S)-2-[(6-chloropyrazin-2-yl)oxy]propyl}carbamate (prepared in analogy to the procedure described for compound 2-8). LRMS (ESI) calculated for $C_{12}H_{18}ClN_3O_3$ $[M+Na]^+$, 310.1; found 310.0.

EXAMPLE 3

Compound 3-1
Trans-4-({6-[5-(1H-pyrazol-4-yl)-1H-pyrrolo[2,3-b]pyridin-3-yl]pyrazin-2-yl}amino)cyclohexanol

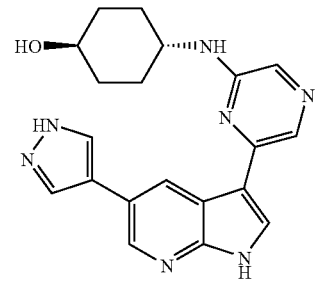

Step 1: Potassium [5-[1-(tert-butoxycarbonyl)-1H-pyrazol-4-yl]-1-(phenylsulfonyl)-1H-pyrrolo[2,3-b]pyridine-3-yl](trifluoro)borate(1-)

To a stirred solution of tert-butyl 4-[1-(phenylsulfonyl)-3-(4,4,5,5-tetramethyl-1,3,2-dioxaborolan-2-yl)-1H-pyrrolo[2,3-b]pyridine-5-yl]-1H-pyrazole-1-carboxylate (4.4 g, 7.9 mmol) in acetone (44 mL) and water (18 mL) was added potassium hydrogen fluoride (3.7 g, 47.6 mmol). The reaction mixture was stirred at room temperature for 1 h. The reaction mixture was concentrated to a crude solid that was then triturated in hot (55° C.) acetone. The mixture was filtered and the filtrate concentrated to a final volume of approximately 40 mL. Diethyl ether (120 mL) was added slowly to promote crystallization. The resulting suspension was cooled in an ice bath for 1 h, then filtered, rinsing the filter cake with diethyl ether/acetone (3:1) to afford potassium [5-[1-(tert-butoxycarbonyl)-1H-pyrazol-4-yl]-1-(phenylsulfonyl)-1H-pyrrolo[2,3-b]pyridine-3-yl]trifluoro)borate(1-) as a grey solid. $^1$H NMR (600 MHz, DMSO-D$_6$) δ 8.70 (s, 1H); 8.59 (d, 1H); 8.26 (d, 1H); 8.05 (d, 1H); 8.01 (dd, 2H); 7.63 (t, 1H); 7.55 (t, 2H); 7.25 (s, 1H); 1.57 (s, 9H).

Step 2:
trans-4[(6-chloropyrazin-2-yl)amino]cyclohexanol 2,6 dichloropyrazine (0.50 g, 3.4 mmol), trans-4-aminocyclohexanol (0.39 g, 3.4 mmol) and cesium carbonate (2.2 g, 6.7 mmol) were added to a round bottom flask and flushed with nitrogen. DMF (4 mL) was then added and the reaction was stirred at 100° C. for 1.5 h. The reaction mixture was cooled to room temperature then diluted with EtOAc (50 mL). The mixture was filtered through celite to remove inorganic salts and the filtrate was concentrated to a crude residue. The residue was purified by silica gel chromatography to afford trans-4-[(6-chloropyrazin-2-yl)amino]cyclohexanol as a yellow oil. LRMS (ESI) calculated for $C_{10}H_{14}ClN_3O$ [M+H]$^+$, 228.1; found 228.1.

Step 3: trans-4-({6-[1-(phenylsulfonyl)-5-(1H-pyrazol-4-yl-1H-pyrrolo[2,3-b]pyridin-3-yl]pyrazin-2-yl)amino}cyclohexanol trans-4-[(6-chloropyrazin-2-yl)amino]cyclohexanol (0.043 g, 0.19 mmol), potassium [5-[1-(tert-butoxycarbonyl)-1H-pyrazol-4-yl]-1-(phenylsulfonyl)-1H-pyrrolo[2,3-b]pyridine-3-yl](trifluoro)borate(1-) (0.10 g, 0.19 mmol), PdCl$_2$(dppf)-CH$_2$Cl$_2$ adduct (7.70 mg, 9.4 μmol) and triethylamine (0.053 mL, 0.38 mmol) were combined in nPrOH/H$_2$O (1:1, 2 mL) and sparged with argon for 5 minutes. The reaction was stirred under nitrogen at 97° C. for 18 h. The reaction mixture was cooled to room temperature and diluted with EtOAc (10 mL). Silica gel was added, and concentrated to a crude residue that was purified by silica gel chromatography (MeOH/CH$_2$Cl$_2$ gradient) to afford trans-4-({6-[1-(phenylsulfonyl)-5-(1H-pyrazol-4-yl)-1H-pyrrolo[2,3-b]pyridin-3-yl]pyrazin-2-yl)amino}cyclohexanol as an orange oil. LRMS (ESI) calculated for $C_{26}H_{25}N_7O_3S$ [M+H]$^+$, 516.2; found 516.1.

Step 4: trans-4-({6-[5-(1H-pyrazol-4-yl)-1H-pyrrolo[2,3-b]pyridin-3-yl]pyrazin-2-yl)amino}cyclohexanol To a stirred solution of trans-4-({6-[1-(phenylsulfonyl)-5-(1H-pyrazol-4-yl)-1H-pyrrolo[2,3-b]pyridin-3-yl]pyrazin-2-yl)amino}cyclohexanol (0.63 g, 0.12 mmol) in MeOH (1.3 mL) was added potassium carbonate (0.051 g, (0.37 mmol). The reaction mixture was stirred at room temperature for 18 h. The reaction mixture was diluted with MeOH (10 mL) and CH$_2$Cl$_2$ (10 mL), silica gel was added and concentrated to a crude residue. The residue was purified by silica gel chromatography (MeOH/CH$_2$Cl$_2$ gradient) to afford trans-4-({6-[5-(1H-pyrazol-4-yl)-1H-pyrrolo[2,3-b]pyridin-3-yl]pyrazin-2-yl)amino}cyclohexanol as a yellow solid. $^1$H NMR (600 MHz, DMSO-D$_6$) δ 12.95 (s, 1H); 11.99 (s, 1H); 8.75 (s, 1H); 8.53 (s, 1H); 8.19 (s, $^1$H); 8.14 (d, 1H); 7.92 (s, 1H); 7.64 (s, 1H); 6.79 (d, 1H); 4.49 (d, 1H); 3.79 (br s, 1H); 3.43 (br s, 1H); 1.83 (br s, 2H); 1.31 (br s, 2H); 1.26 (q, 4H). LRMS (ESI) calculated for $C_{20}H_{21}N_7O$ [M+H]$^+$, 376.2; found 376.1.

The compounds listed below in Table 3 were prepared in analogy to the preparation of Compound 3-1 starting from potassium [5-[1-(tert-butoxycarbonyl)-1H-pyrazol-4-yl]-1-(phenylsulfonyl)-1H-pyrrolo[2,3-b]pyridine-3-yl](trifluoro)borate(1-), and utilizing the appropriate substituted-6-chloropyrazine in the requisite Suzuki coupling described above. Unless otherwise indicated, the compounds were isolated as the free base.

TABLE 3

| Compound | Structure | Name | [M + H]+ calc | [M + H]+ obs |
|---|---|---|---|---|
| 3-2 | 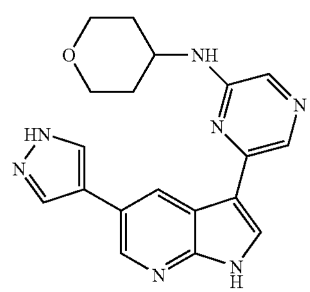 | 6-[5-(1H-pyrazol-4-yl)-1H-pyrrolo[2,3-b]pyridin-3-yl-N-(tetrahydro-2H-pyran-5-yl)pyrazin-2-amine | 362.2 | 362.1 |
| 3-3 | 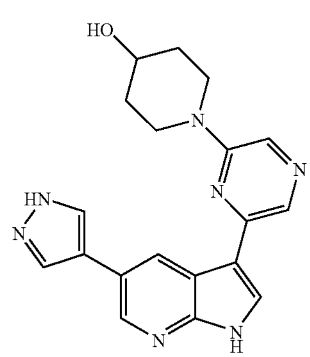 | 1-{6-[5-(1H-pyrazol-4-yl)-1H-pyrrolo[2,3-b]pyridin-3-yl]pyrazin-2-yl}piperdin-4-ol | 362.2 | 362.1 |

TABLE 3-continued

| Compound | Structure | Name | [M + H] + calc | [M + H] + obs |
|---|---|---|---|---|
| 3-4 | 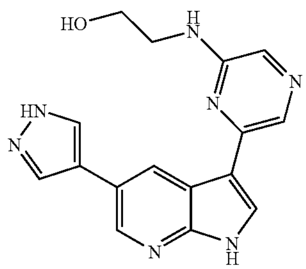 | 2-({6-[5-(1H-pyrazol-4-yl)-1H-pyrrolo[2,3-b]pyridin-3-yl]pyrazin-2-yl}amino)ehthanol | 322.1 | 322.1 |
| 3-5 | 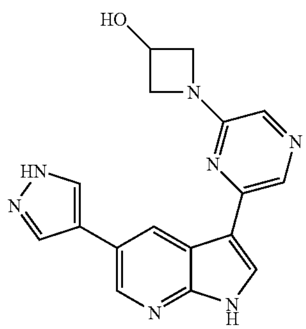 | 1-{6-[5-(1H-pyrazol-4-yl)-1H-pyrrolo[2,3-b]pyridin-3-yl]pyrazin-2-yl}azetidin-3-ol | 334.1 | 334.1 |
| 3-6 | 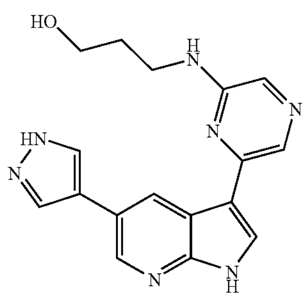 | 3-({6-[5-(1H-pyrazol-4-yl)-1H-pyrrolo[2,3-b]pyridin-3-yl]pyrazin-2-yl}amino)propan-1-ol | 336.2 | 336.1 |
| 3-7 | 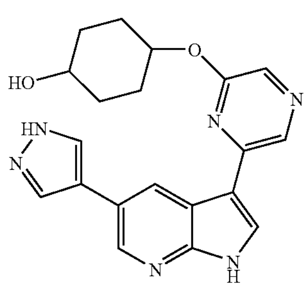 | 4-({6-[5-(1H-pyrazol-4-yl)-1H-pyrrolo[2,3-b]pyridin-3-yl]pyrazin-2-yl}oxy)cyclohexanol | 377.2 | 337.1 |

Compound 3-2 was prepared using 6-chloro-N-(tetrahydro-2H-pyran-4-yl)pyrazin-2-amine (prepared in analogy to the procedure described for Compound 3-1). LRMS (ESI) calculated for $C_9H_{12}ClN_3O$ [M+H]$^+$, 214.1; found 214.1.

Compound 3-3 was prepared using 1-(6-chloropyrazin-2-yl)piperidin-4-ol (prepared in analogy to the procedure described for Compound 3-1). LRMS (ESI) calculated for $C_9H_{12}ClN_3O$ [M+H]$^+$, 214.1; found 214.0.

Compound 3-4 was prepared using 2-[(6-chloropyrazin-2-yl)amino]ethanol (prepared in analogy to the procedure described for Compound 3-1). LRMS (ESI) calculated for $C_6H_8ClN_3O$ [M+H]$^+$, 174.0; found 174.0.

Compound 3-5 was prepared using 1-(6-chloropyrazin-2-yl)azetidin-3-ol (prepared in analogy to the procedure described for Compound 3-1). LRMS (ESI) calculated for $C_7H_8ClN_3O$ [M+H]$^+$, 186.0; found 186.0.

Compound 3-6 was prepared using 3-[(6-chloropyrazin-2-yl)amino]propan-1-ol (prepared in analogy to the procedure described for Compound 3-1). LRMS (ESI) calculated for $C_7H_{10}ClN_3O$ [M+H]$^+$, 188.1; found 188.0.

Compound 3-7 was prepared using 4-[(6-chloropyrazin-2-yl)oxy]cyclohexanol (prepared in analogy to the procedure described for Compound 3-1). LRMS (ESI) calculated for $C_7H_{10}ClN_3O$ [M+H]$^+$, 229.1; found 229.0.

EXAMPLE 4

Compound 4-1

5-(1-ethyl-1H-pyrazol-4-yl)-3-[6-(piperidin-4-yloxy)pyrazin-2-yl]-1H-pyrrolo[2,3-b]pyridine

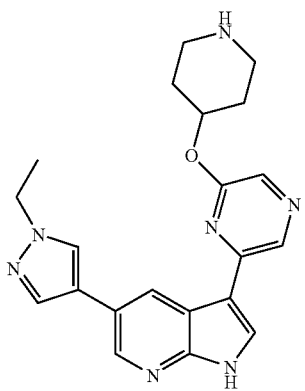

Step 1: tert-butyl 4-({6-[5-(1-ethyl-1H-pyrazol-4-yl)-1-(phenylsulfonyl)-1H-pyrrolo[2,3-b]pyridine-3-yl]pyrazin-2-yl}oxy)piperidine-1-carboxylate To a stirred solution of tert-butyl 4-({6-[1-(phenylsulfonyl)-5-(1H-pyrazol-4-yl)-1H-pyrrolo[2,3-b]pyridine-3-yl]pyrazin-2-yl}oxy)piperidine-1-carboxylate (0.075 g, 0.13 mmol) and iodoethane (11 pt, 0.14 mmol) in DMF (1.3 mL) at 0° C. was added sodium hydride (60% mineral oil dispersion; 6.0 mg, 0.15 mmol). The reaction mixture was stirred at 0° C. for 1 h then quenched with aqueous saturated sodium bicarbonate (5 mL). The reaction mixture was extracted with EtOAc (3×10 mL). The combined organic layers were dried over magnesium sulfate, filtered and concentrated. The crude residue was purified by silica gel chromatography (EtOAc/Hexanes gradient) to afford tert-butyl 4-({6-[5-(1-ethyl-1H-pyrazol-4-yl)-1-(phenylsulfonyl)-1H-pyrrolo[2,3-b]pyridine-3-yl]pyrazin-2-yl}oxy)piperidine-1-carboxylate as a yellow oil. LRMS (ESI) calculated for $C_{32}H_{35}N_7O_5S$ $[M+H]^+$, 630.2; found 630.2.

5-(1-ethyl-1H-pyrazol-4-yl)-3-[6-(piperidin-4-yloxy)pyrazin-2-yl]-1H-pyrrolo[2,3-b]pyridine was prepared by the method shown in Scheme 1. $^1$H NMR (600 MHz, DMSO-D$_6$) δ 9.02 (br s, 1H); 8.91 (br s, 1H); 8.77 (s, 1H); 8.69 (d, 1H); 8.61 (d, 1H); 8.50 (s, 1H); 8.13 (s, 1H); 8.04 (s, 1H); 5.47 (m, 1H); 4.34 (q, 2H); 3.23 (m, 2H); 3.10 (m, 2H); 2.22 (m, 2H); 2.05 (m, 2H); 1.43 (t, 3H). LRMS (ESI) calculated for $C_{21}H_{23}N_7O$ $[M+H]^+$, 390.5; found 390.2.

The compounds listed below in Table 4 were prepared in analogy to the preparation of Compound 4-1 starting from tert-butyl 4-({6-[1-(phenylsulfonyl)-5-(1H-pyrazol-4-yl)-1H-pyrrolo[2,3-b]pyridine-3-yl]pyrazin-2-yl}oxy)piperidine-1-carboxylate as described above. Unless otherwise indicated, the compounds were isolated as their hydrochloride salts.

TABLE 4

| Compound | Structure | Name | [M + H] + calc | [M + H] + obs |
|---|---|---|---|---|
| 4-2 | 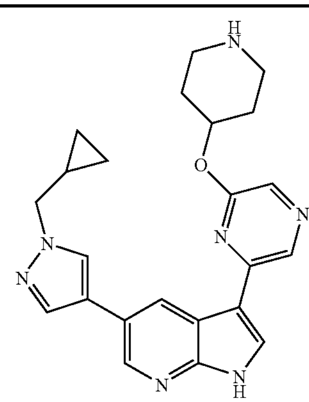 | 5-[1-(cyclopropylmethyl)-1H-pyrazol-4-yl]-3-[6-(piperidin-4-yloxy)pyrazin-2-yl]-1H-pyrrolo[2,3-b]pyridine | 416.2 | 416.2 |
| 4-3 | 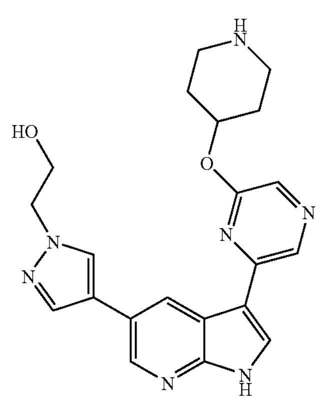 | 2-(4-{3-[6-(piperidin-4-yloxy)pyrazin-2-yl]-1H-pyrrolo[2,3-b]pyridine-5-yl}-1H-pyrazol-1-yl)ethanol | 406.2 | 406.1 |

TABLE 4-continued

| Compound | Name | [M + H]+ calc | [M + H]+ obs |
|---|---|---|---|
| 4-4 | 3-[6-(piperidin-4-yloxy)pyrazin-2-yl]-5-[1-(2,2,2-trifluoroethyl)-1H-pyrazol-4-yl]-1H-pyrrolo[2,3-b]pyridine | 444.2 | 444.1 |
| 4-5 | 3-[6-(piperidin-4-yloxy)pyrazin-2-yl]-1-(2,2,2-trifluoroethyl)-5-[1-(2,2,2-trifluoroethyl)-1H-pyrazol-4-yl]-1H-pyrrolo[2,3-b]pyridine | 526.2 | 526.1 |

Compound 4-2 was prepared using bromomethyl cyclopropane as the alkylating agent in Step 1 to afford tert-butyl 4-({6-[5-[1-(cyclopropylmethyl)-1H-pyrazol-4-yl]-1-(phenylsulfonyl)-1H-pyrrolo[2,3-b]pyridin-3-yl]pyrazin-2-yl}oxy)piperidine-1-carboxylate. LRMS (ESI) calculated for $C_{34}H_{37}N_7O_5S$ [M+H]+, 656.3; found 656.2.

Compound 4-3 was prepared using ethyl bromoacetate as the alkylating agent in Step 1 to afford tert-butyl 4-({6-[5-[1-(2-ethoxy-2-oxoethyl)-1H-pyrazol-4-yl]-1-(phenylsulfonyl)-1H-pyrrolo[2,3-b]pyridin-3-yl]pyrazin-2-yl}oxy)piperidine-1-carboxylate which was then reduced to afford tert-butyl 4-({6-[5-[1-(2-hydroxyethyl)-1H-pyrazol-4-yl]-1-(phenylsulfonyl)-1H-pyrrolo[2,3-b]pyridin-3-yl]pyrazin-2-yl}oxy)piperidine-1-carboxylate:

tert-butyl 4-({6-[5-[1-(2-hydroxyethyl)-1H-pyrazol-4-yl]-1-(phenylsulfonyl)-1H-pyrrolo[2,3-b]pyridin-3-yl]pyrazin-2-yl}oxy)piperidine-1-carboxylate To a stirred solution of tert-butyl 4-({6-[5-[1-(2-ethoxy-2-oxoethyl)-1H-pyrazol-4-yl]-1-(phenylsulfonyl)-1H-pyrrolo[2,3-b]pyridin-3-yl]pyrazin-2-yl}oxy)piperidine-1-carboxylate (0.10 g, 0.15 mmol) in tetrahydrofuran (2 mL) was added lithium aluminium hydride (11 mg, 0.29 mmol) (CAUTION: GAS EVOLUTION). The reaction mixture was stirred at room temperature for 2.5 h then cooled in an ice bath. Sodium sulfate decahydrate (0.32 mL, 1.5 mmol) was added to the reaction mixture slowly (CAUTION: GAS EVOLUTION). The reaction mixture was warmed to room temperature and filtered through celite. The filtrate was concentrated to a crude solid and purified by reverse phase HPLC to afford tert-butyl 4-({6-[5-[1-(2-hydroxyethyl)-1H-pyrazol-4-yl]-1-(phenylsulfonyl)-1H-pyrrolo[2,3-b]pyridin-3-yl]pyrazin-2-yl}oxy)piperidine-1-carboxylate. LRMS (ESI) calculated for $C_{32}H_{35}N_7O_6S$ [M+H]+, 646.2; found 646.2.

Compound 4-4 was prepared using 2,2,2-trifluoroethyl trifluoromethanesulfonate as the alkylating agent in Step 1 to afford tert-butyl 4-[(6-{1-(phenylsulfonyl)-5-[1-(2,2,2-trifluoroethyl)-1H-pyrazol-4-yl]-1H-pyrrolo[2,3-b]pyridin-3-yl}pyrazin-2-yl)oxy]piperidine-1-carboxylate. LRMS (ESI) calculated for $C_{32}H_{32}F_3N_7O_5S$ [M+H]+, 684.2; found 684.1.

Compound 4-5 was prepared using tert-butyl 4-[(6-{1-(2,2,2-trifluoroethyl)-5-[1-(2,2,2-trifluoroethyl)-1H-pyrrolo[2,3-b]pyridin-3-yl}pyrazin-2-yl)oxy]piperidine-1-carboxylate LRMS (ESI) calculated for $C_{28}H_{29}F_6N_7O_3$ [M+Na]+, 648.2; found 648.1. Isolated as a side product from the synthesis of tert-butyl 4-[(6-{1-(phenylsulfonyl)-5-[1-(2,2,2-trifluoroethyl)-1H-pyrazol-4-yl]-1H-pyrrolo[2,3-b]pyridin-3-yl}pyrazin-2-yl)oxy]piperidine-1-carboxylate.

EXAMPLE 5

Compound 5-1

5-(1H-pyrazol-4-yl)-3-(6-{[3-(trifluoromethyl)azetidin-3-yl]oxy}pyrazin-2-yl)-1H-pyrrolo[2,3-b]pyridine

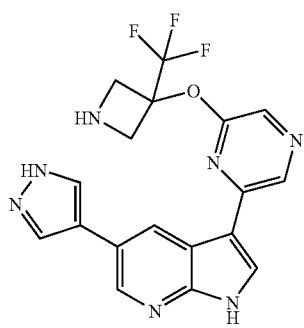

Step 1: tert-butyl 3-oxoazetidine-1-carboxylate

To a stirred solution of 1-boc-3-(hydroxyl)azetine (1.0 g, 5.8 mmol) and triethylamine (1.6 mL, 12 mmol) in $CH_2Cl_2$ (10 mL) and DMSO (4 mL) at 0° C. was added pyridine sulfur trioxide (1.8 g, 12 mmol). The reaction was allowed to warm to room temperature. After 18 h, the reaction mixture was partitioned between $CH_2Cl_2$ (100 mL) and 1M aqueous citric acid solution (100 mL). The organic layer was washed with brine, dried over magnesium sulfate, filtered and concentrated to afford tert-butyl 3-oxoazetidine-1-carboxylate as a crude oil. $^1$H NMR (600 MHz, DMSO-$D_6$) δ 4.67 (s, 4H); 1.47 (s, 9H).

Step 2: tert-butyl 3-hydroxy-3-(trifluoromethyl)azetidine-1-carboxylate

To a stirred solution of tert-butyl 3-oxoazetidine-1-carboxylate (0.50 g, 2.9 mmol) and (trifluoromethyl)trimethylsilane (0.65 mL, 4.4 mmol) in tetrahydrofuran (5 mL) at 0° C. was added tetramethylammonium fluoride (0.014 g, 0.15 mmol). The reaction mixture was warmed to room temperature. After 1 h, the reaction mixture was poured into a 0.5M aqueous ammonium chloride solution (25 mL) and extracted with diethyl ether (25 mL). The organic layer was dried over magnesium sulfate, filtered and concentrated to a crude oil. The crude oil was dissolved in tetrahydrofuran (5 mL). A 1M aqueous citric acid solution (5 mL) was added and the mixture was stirred for 1 h. The reaction mixture was partitioned between diethyl ether (25 mL) and water (10 mL). The organic layer was dried over magnesium sulfate, filtered and concentrated to a crude oil. The residue was purified by silica gel chromatography (EtOAc/Hexanes gradient) to afford tert-butyl 3-hydroxy-3-(trifluoromethyl)azetidine-1-carboxylate as a white solid. $^1$H NMR (600 MHz, DMSO-$D_6$) δ 4.17 (d, 2H); 3.91 (d, 2H); 1.43 (s, 9H).

Step 3: tert-butyl 3-[(6-chloropyrazine-2-yl)oxy]-3-(trifluoromethyl)azetidine-1-carboxylate To a stirred solution of tert-butyl 3-hydroxy-3-(trifluoromethyl)azetidine-1-carboxylate (0.37 g, 1.5 mmol) and 2,6-dichloropyrazine (0.23 g, 1.5 mmol) in DMF (5 mL) at 0° C. was added sodium hydride (60% mineral oil dispersion; 0.073 g, 1.8 mmol). The reaction mixture was allowed to warm to room temperature. After 15 minutes, the reaction mixture was partitioned between EtOAc (50 mL) and brine (50 mL). The organic layer was washed with additional brine (50 mL). The first aqueous layer was back-extracted with EtOAc (50 mL). The combined organic layers were dried over magnesium sulfate, filtered and concentrated. The crude residue was purified by silica gel chromatography (EtOAc/Hexanes gradient) to afford tert-butyl 3-[(6-chloropyrazine-2-yl)oxy]-3-(trifluoromethyl)azetidine-1-carboxylate. LRMS calculated for $C_{13}H_{15}ClF_3N_3O_3[M+H]^+$, 354.1; found 298.0 $[M-tButyl+H]^+$. $^1$H NMR (600 MHz, DMSO-$D_6$) δ 8.50 (s, 1H); 8.46 (s, 1H); 4.53 (br s, 2H); 4.20 (br d, 2H); 1.37 (s, 9H).

5-(1H-pyrazol-4-yl)-3-(6-{[3-(trifluoromethyl)azetidin-3-yl]oxy}pyrazin-2-yl)-1H-pyrrolo[2,3-b]pyridine was prepared by the method shown in Scheme 1. $^1$H NMR (600 MHz, DMSO-$D_6$) δ 12.38 (s, 1H); 9.69 (br s, 1H); 9.39 (br s, 1H); 9.01 (s, 1H); 8.61 (d, 1H); 8.50 (d, 1H); 8.36 (d, 1H); 8.25 (s, 1H); 8.11 (s, 2H); 4.73 (m, 2H); 4.65 (m, 2H). LRMS (ESI) calculated for $C_{18}H_{14}F_3N_7O$ $[M+H]^+$, 402.1; found 402.1.

The compounds listed below in Table 5 were prepared in analogy to the preparation of Compound 5-1 from potassium [5-[1-(tert-butoxycarbonyl)-1H-pyrazol-4-yl]-1-(phenylsulfonyl)-1H-pyrrolo[2,3-b]pyridin-3-yl](trifluoro)borate(1-) and utilizing the appropriate substituted-6-chloropyrazine in the requisite Suzuki coupling. Unless otherwise indicated, the compounds were isolated as their hydrochloride salts.

TABLE 5

| Compound | Structure | Name | [M + H] + calc | [M + H] + obs |
|---|---|---|---|---|
| 5-2 | ![structure] | 3,3,3-trifluoro-2-({6-[5-(1H-pyrazol-4-yl)-1H-pyrrolo[2,3-b]pyridin-3-yl]pyrazin-2-yl}oxy)propan-1-amine | 390.1 | 390.1 |

TABLE 5-continued

| Compound | Structure | Name | [M + H] + calc | [M + H] + obs |
|---|---|---|---|---|
| 5-3 | 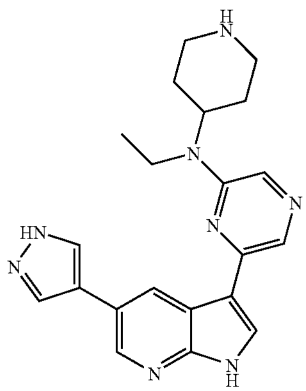 | N-ethyl-N-piperidin-4-yl-6-[5-(1H-pyrazol-4-yl)-1H-pyrrolo[2,3-b]pyridin-3-yl]pyrazin-2-amine | 389.2 | 389.2 |
| 5-4 | 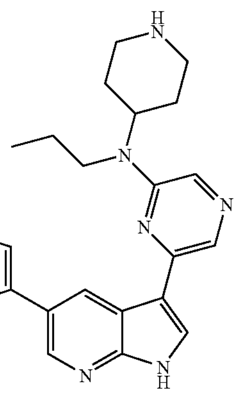 | N-piperidin-4-yl-N-propyl-6-[5-(1H-pyrazol-4-yl)-1H-pyrrolo[2,3-b]pyridin-3-yl]pyrazin-2-amine | 403.2 | 403.1 |
| 5-5 | 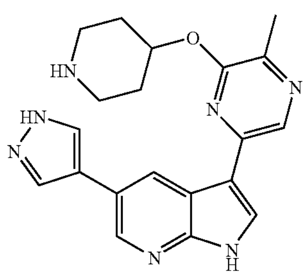 | 3-[5-methyl-6-(piperidin-4-yloxy)pyrazin-2-yl]-5-(1H-pyrazol-4-yl)-1H-pyrrolo[2,3-b]pyridine | 376.2 | 376.2 |
| 5-6 | 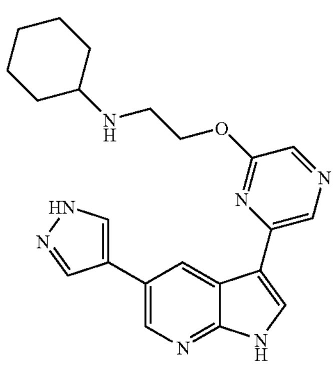 | N-[2-({6-[5-(1H-pyrazol-4-yl)-1H-pyrrolo[2,3-b]pyridin-3-yl]pyrazin-2-yl}oxy)ethyl]cyclohexanamine | 404.2 | 404.2 |

Compound 5-2 was prepared using 3-azido-1,1,1-trifluoropropan-2-ol in Step 3 to afford 2-[1-(azidomethyl)-2,2,2-trifluoroethoxy]-6-chloropyrazine; LRMS (ESI) calculated for $C_7H_5ClF_3N_5O$ [M+H]$^+$, 268.0; found 268.0. 3-{6-[1-(azidomethyl)-2,2,2-trifluoroethoxy]pyrazin-2-yl}-5-(1H-pyrazol-4-yl)-1H-pyrrolo[2,3-b]pyridine was prepared in analogy to Scheme 1 before conversion to tert-butyl [3,3,3-trifluoro-2-({6-[5-(1H-pyrazol-4-yl)-1H-pyrrolo[2,3-b]pyridin-3-yl]pyrazin-2-yl}oxy)propyl]carbamate as described below.

3-azido-1,1,1-trifluoropropan-2-ol

Synthesis Adapted from the Following Reference:
Ramachandran, P. V; Gong, B.; Brown, H. C. *J. Org. Chem.* 1995, 60, 41-46.

To a stirred solution of 1,1,1-trifluoro-2,3-epoxypropane (2.0 g, 18 mmol) in 70% ethanol (20 mL) was added ammonium chloride (1.9 g, 36 mmol) followed by sodium azide (2.3 g, 36 mmol). The reaction mixture was stirred at room temperature. After 6 h, the reaction mixture was partitioned between water (100 mL) and diethyl ether (100 mL). The organic layer was washed with additional water (100 mL). The first aqueous layer was back-extracted with diethyl ether (100 mL). The combined organic layers were dried over magnesium sulfate, filtered and concentrated to give 3-azido-1,1,1-trifluoropropan-2-ol as a crude oil. $^1$H NMR (600 MHz, DMSO-D$_6$) δ 4.14 (m, 1H); 3.58-3.49 (m, 2H); 2.58 (d, 1H).

tert-butyl[3,3,3-trifluoro-2-({6-[5-(1H-pyrazol-4-yl)-1H-pyrrolo[2,3-b]pyridin-3-yl]pyrazin-2-yl}oxy)propyl]carbamate A stirred solution of 3-{6-[1-(azidomethyl)-2,2,2-trifluoroethoxy]pyrazin-2-yl}-5-(1H-pyrazol-4-yl)-1H-pyrrolo[2,3-b]pyridine (0.014 g, 0.034 mmol) and acetic acid (1.9 µL, 0.034 mmol) in methanol (0.4 mL) was sparged with nitrogen. To this solution was added a catalytic amount of Pd/C, and purged further with nitrogen. The resulting suspension was stirred under hydrogen (balloon pressure) for 2 h. The reaction mixture was filtered. To this solution was added di-tert-butyl dicarbonate (0.011 g, 0.051 mmol). After 1 h, the reaction mixture was concentrated to afford tert-butyl[3,3,3-trifluoro-2-({6-[5-(1H-pyrazol-4-yl)-1H-pyrrolo[2,3-b]pyridin-3-yl]pyrazin-2-yl}oxy)propyl]carbamate as a crude oil. LRMS (ESI) calculated for $C_{22}H_{22}F_3N_7O_3$ [M+H]$^+$, 490.2; found 490.1.

Compound 5-3 was prepared using tert-butyl 4-[(6-chloropyrazin-2-yl)(ethyl)amino]piperidine-1-carboxylate in Step 3.

Step 1: tert-butyl 4[(6-chloropyrazin-2-yl)amino]piperidine-1-carboxylate

To a stirred solution of 2,6-dichloropyrazine (5.0 g, 34 mmol) and 4-amino-1-boc-piperidine (6.7 g, 34 mmol) in DMF (67 mL) was added cesium carbonate (22 g, 67 mmol). The reaction mixture was stirred at 100° C. After 4 h, the reaction was quenched with saturated aqueous sodium bicarbonate (100 mL) and extracted with EtOAc (3×100 mL). The combined organic layers were dried over magnesium sulfate, filtered and concentrated. The crude residue was purified by silica gel chromatography (EtOAc/Hexanes gradient) to afford tert-butyl 4-[(6-chloropyrazin-2-yl)amino]piperidine-1-carboxylate as a yellow solid. LRMS (ESI) calculated for $C_{14}H_{21}ClN_4O_2$ [M+Na]$^+$, 335.1; found 335.1.

Step 2: tert-butyl 4-[(6-chloropyrazin-2-yl)(ethyl)amino]piperidine-1-carboxylate To a stirred solution of tert-butyl 4-[(6-chloropyrazin-2-yl)amino]piperidine-1-carboxylate (0.20 g, 0.64 mmol) in tetrahydrofuran (3 mL) at −70° C. was added iodoethane (0.26 mL, 3.2 mmol) and NaHMDS (1M solution in THF; 1.3 mL, 1.3 mmol). The reaction mixture was warmed to room temperature. Iodoethane (0.26 mL, 3.2 mmol) and NaHMDS (1M solution in THF; 1.3 mL, 1.3 mmol) were added. The reaction mixture was stirred at 65° C. After 18 h, the reaction was quenched with saturated aqueous ammonium chloride (25 mL) and extracted with EtOAc (3×25 mL). The organic layers were combined, dried over magnesium sulfate, filtered and concentrated. The crude residue was purified by silica gel chromatography (EtOAc/Hexanes gradient) to afford tert-butyl 4-[(6-chloropyrazin-2-yl)(ethyl)amino]piperidine-1-carboxylate as a yellow solid. LRMS (ESI) calculated for $C_{16}H_{25}ClN_4O_2$ [M$^+$Na]$^+$, 363.2; found 363.1.

Compound 5-4 was prepared using tert-butyl 4-[(6-chloropyrazin-2-yl)(propyl)amino)piperidine-1-carboxylate in Step 3.

tert-butyl 4-[(6-chloropyrazin-2-yl)(propyl)amino]piperidine-1-carboxylate

To a stirred solution of tert-butyl 4-[(6-chloropyrazin-2-yl)amino]piperidine-1-carboxylate (0.20 g, 0.64 mmol) in tetrahydrofuran (3 mL) at 0° C. was added 1-iodopropane (1 mL, 10 mmol) and sodium hyrdride (0.051 g, 1.3 mmol). The reaction mixture was warmed to room temperature then stirred at 60° C. After 1.5 h, the reaction mixture was cooled to room temperature and quenched with water (10 mL). The reaction mixture was extracted with EtOAc (3×25 mL). The combined organic layers were washed with brine (10 mL), dried over magnesium sulfate, filtered and concentrated. The crude residue was purified by silica gel chromatography (EtOAc/Hexanes gradient) to afford tert-butyl 4-[(6-chloropyrazin-2-yl)(propyl)amino]piperidine-1-carboxylate as a yellow oil. LRMS (ESI) calculated for $C_{17}H_{27}ClN_4O_2$ [M+Na]$^+$, 377.2; found 377.1.

Compound 5-5 was prepared using 3,5-dichloro-2-methylpyrazine and 1-boc-4-hydroxypiperidine in Step 3.

3,5-dichloro-2-methylpyrazine

To a solution of n-butyl lithium (1.6M in hexanes; 29 mL, 47 mmol) in tetrahydrofuran (200 mL) at −30° C. was added 2,2,6,6-tetramethylpiperidine (8.6 mL, 50 mmol). This solution was allowed to warm to 0° C. over 20 minutes then cooled to −78° C. To this solution was added a solution of 2,6-dichloropyrazine (5 g, 34 mmol) in tetrahydrofuran (200 mL) dropwise via cannula. After 30 minutes, iodomethane (21 mL, 340 mmol.) was added. After 1 h, the reaction mixture was quenched with a mixture of EtOH (25 mL), THF (25 mL) and 1N aqueous HCl (5 mL). The reaction mixture was allowed to warm to room temperature then concentrated to a crude oil. The crude oil was partitioned between water (500 mL) and CH$_2$Cl$_2$ (500 mL). The organic layer was washed with brine (250 mL). The first aqueous layer was back-extracted with CH$_2$Cl$_2$ (500 mL). The combined organic layers were dried over sodium sulfate, filtered and concentrated. The crude residue was purified by silica gel chromatography (EtOAc/Hexanes gradient) to afford 3,5-dichloro-2-methylpyrazine as a yellow oil. LRMS (ESI) calculated for $C_5H_4Cl_2N_2$ [M+H]$^+$, 163.0; found 163.1.

Compound 5-6 was prepared using N-{2-[(6-chloropyrazin-2-yl)oxy]ethyl}cyclohexanamine in Step 3.

N-{2-[(6-chloropyrazin-2-yl)oxy]ethyl}cyclohexanamine

To a stirred solution of n-cyclohexylethanolamine (0.48 g, 3.4 mmol) and 2,6-dichloropyrazine (0.50 g, 3.4 mmol) in toluene (17 mL) was added 3,4,7,8-tetramethyl-1,10-phenanthroline (7.9 mg, 0.034 mmol), copper iodide (0.032 g, 0.17 mmol) and cesium carbonate (2.2 g, 6.7 mmol). The reaction mixture was stirred at 100° C. After 18 h, the reaction mixture was cooled to room temperature, diluted with EtOAc (50 mL), filtered through celite and concentrated. The crude residue was purified by silica gel chromatography (EtOAc/Hexanes gradient) to afford N-{2-[(6-chloropyrazin-2-yl)oxy]ethyl}cyclohexanamine as an orange oil. LRMS (ESI) calculated for $C_{12}H_{18}ClN_3O$ [M+H]$^+$, 256.1; found 256.1.

What is claimed is:

1. A compound of formula (I):

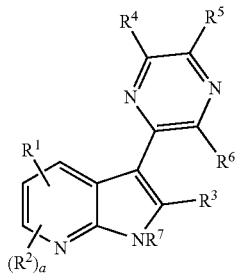

wherein:
a is 0, 1 or 2;
each of $R^1$ and $R^2$ is independently hydroxy, cyano, halogen, $C_{1-6}$alkyl, $C_{2-10}$alkenyl, halo$C_{1-6}$alkyl, hydroxy $C_{1-6}$alkyl, $C_{1-6}$alkylcarbonyl, $C_{1-6}$alkoxy, halo$C_{1-6}$alkoxy, $C_{1-6}$alkoxycarbonyl, carboxy, nitro, $NR^xR^y$, $CONR^xR^y$, $NR^x(CONR^xR^y)$, $S(O)_rNR^xR^y$ or a ring which is: $C_{6-10}$aryl, $C_{6-10}$aryloxy, $C_{6-10}$aryl$C_{1-6}$ alkyl, $C_{6-10}$arylcarbonyl, $C_{3-10}$cycloalkyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 N atoms or a 7-15 membered unsaturated, partially saturated or saturated heterocyclic ring containing 1, 2, 3 or 4 heteroatoms independently selected from N, O and S; optionally substituted by one or more groups independently selected from $R^a$;
$R^3$ is hydrogen or $C_{1-6}$alkyl;
$R^4$ is hydrogen, -L-$R^b$ or -M-$R^c$;
each of $R^5$, $R^6$ and $R^7$ is independently selected from hydrogen, hydroxy, cyano, halogen, $C_{1-6}$alkyl, $C_{2-10}$alkenyl, halo$C_{1-6}$alkyl, hydroxy$C_{1-6}$alkyl, $C_{1-6}$alkylcarbonyl, $C_{1-6}$alkoxy, halo$C_{1-6}$alkoxy, $C_{1-6}$alkoxycarbonyl, carboxy, nitro, $NR^xR^y$ or a ring which is: $C_{6-10}$aryl, $C_{6-10}$aryl$C_{1-6}$alkyl, $C_{3-10}$cycloalkyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 nitrogen atoms or a 7-15 membered unsaturated, partially saturated or saturated heterocyclic ring containing 1, 2, 3 or 4 heteroatoms independently selected from N, O and S; any of which rings being optionally substituted by one or more groups independently selected from hydroxy, cyano, halogen, $C_{1-6}$alkyl, $C_{1-6}$alkoxy, $C_{2-10}$alkenyl, halo$C_{1-6}$alkyl, amino, $C_{1-6}$alkylamino and di($C_{1-6}$alkyl)amino;
each of L and M is a direct bond, —O(CR'R'')$_b$[N(R$^z$)]$_c$— or —N(R$^z$)(CR'R'')$_b$—;
b is 0, 1, 2, 3 or 4;
c is 0 or 1;
r is 0, 1 or 2;

each $R^a$ is independently selected from hydroxy, oxo, cyano, halogen, $C_{1-6}$alkyl, $C_{2-10}$alkenyl, halo$C_{1-6}$alkyl, $C_{1-6}$alkylcarbonyl, $C_{1-6}$alkoxy, halo$C_{1-6}$alkoxy, hydroxy$C_{1-6}$alkyl, $C_{1-6}$alkoxycarbonyl, carboxy, $NR^xR^y$ or a ring which is: $C_{6-10}$aryl, $C_{6-10}$aryl$C_{1-6}$alkyl, $C_{3-10}$cycloalkyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 nitrogen atoms or a 7-15 membered unsaturated, partially saturated or saturated heterocyclic ring containing 1, 2, 3 or 4 heteroatoms independently selected from N, O and S; any of which rings being optionally substituted by one or more groups independently selected from hydroxy, cyano, halogen, $C_{1-6}$alkyl, $C_{1-6}$alkoxy, $C_{2-10}$alkenyl, halo$C_{1-6}$alkyl, amino, $C_{1-6}$alkylamino and di($C_{1-6}$alkyl)amino;
$R^b$ is hydroxy, cyano, halogen, $C_{1-6}$alkyl, $C_{2-10}$alkenyl, halo$C_{1-6}$alkyl, hydroxy$C_{1-6}$alkyl, $C_{1-6}$alkylcarbonyl, $C_{1-6}$alkoxy, halo$C_{1-6}$alkoxy, $C_{1-6}$alkoxycarbonyl, carboxy, nitro or $NR^xR^y$;
$R^c$ is $C_{3-10}$cycloalkyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O, and S, not more than one heteroatom of which is O or S, a 6 membered heteroaromatic ring containing 1, 2 or 3 N atoms or a 7-15 membered unsaturated, partially saturated or saturated heterocyclic ring containing 1, 2, 3 or 4 heteroatoms independently selected from N, O and S; optionally substituted by one or more groups independently selected from $R^d$;
each $R^d$ is independently selected from hydroxy, oxo, cyano, halogen, $C_{1-6}$alkyl, $C_{2-10}$alkenyl, halo$C_{1-6}$alkyl, $C_{1-6}$alkylcarbonyl, $C_{1-6}$alkoxy, halo$C_{1-6}$alkoxy, hydroxy$C_{1-6}$alkyl, $C_{1-6}$alkoxycarbonyl, carboxy, $NR^xR^y$ or a ring which is: $C_{6-10}$aryl, $C_{6-10}$aryl$C_{1-6}$alkyl, $C_{3-10}$cycloalkyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 nitrogen atoms or a 7-15 membered unsaturated, partially saturated or saturated heterocyclic ring containing 1, 2, 3 or 4 heteroatoms independently selected from N, O and S; any of which rings being optionally substituted by one or more groups independently selected from hydroxy, cyano, halogen, $C_{1-6}$alkyl, $C_{1-6}$alkoxy, $C_{2-10}$alkenyl, halo$C_{1-6}$alkyl, amino, $C_{1-6}$alkylamino and di($C_{1-6}$alkyl)amino;
each of R' and R'' is independently hydrogen, $C_{1-6}$alkyl, halogen, hydroxy or halo$C_{1-6}$alkyl;
each of $R^x$ and $R^y$ is independently hydrogen, $C_{1-6}$alkyl, $C_{1-6}$alkylcarbonyl, halo$C_{1-6}$alkyl or hydroxy$C_{1-6}$alkyl;
$R^z$ is hydrogen or $C_{1-6}$alkyl;
or a pharmaceutically acceptable salt, stereoisomer or tautomer thereof.

2. A compound of claim 1 of formula (II):

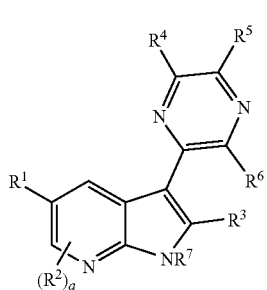

(II)

wherein:
R¹ is azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, and S, not more than one heteroatom of which is O or S, a 6 membered heteroaromatic ring containing 1, 2 or 3 N atoms or a 7-15 membered unsaturated, partially saturated or saturated heterocyclic ring containing 1, 2, 3 or 4 heteroatoms independently selected from N, O and S; optionally substituted by one or more groups independently selected from $R^a$;

or a pharmaceutically acceptable salt, stereoisomer or tautomer thereof.

3. A compound of claim 1 of formula (III):

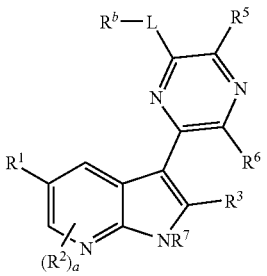

(III)

wherein:
L is —O(CR'R^w)_b— or —N(R^z)(CR'R^w)_b—;
$R^l$ is azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 N atoms or a 7-15 membered unsaturated, partially saturated or saturated heterocyclic ring containing 1, 2, 3 or 4 heteroatoms independently selected from N, O and S; optionally substituted by one or more groups independently selected from $R^a$;

or a pharmaceutically acceptable salt, stereoisomer or tautomer thereof.

4. A compound of claim 1 of formula (IV):

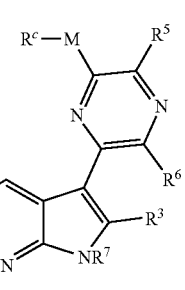

(IV)

wherein:
M is a direct bond, —O—, —N(R^z)— or —O(CR'R^w)_bN(R^z)—;
R¹ is azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 N atoms or a 7-15 membered unsaturated, partially saturated or saturated heterocyclic ring containing 1, 2, 3 or 4 heteroatoms independently selected from N, O and S; optionally substituted by one or more groups independently selected from $R^a$;

or a pharmaceutically acceptable salt, stereoisomer or tautomer thereof.

5. A compound of claim 1 wherein $R^7$ is hydrogen, $C_{1-6}$alkyl or halo$C_{1-6}$alkyl.

6. A compound of claim 1 wherein each of $R^5$ and $R^6$ is independently hydrogen or $C_{1-6}$alkyl.

7. A compound of claim 1 selected from:
5-(1-methyl-1H-pyrazol-4-yl)-3-(6-piperazin-1-ylpyrazin-2-yl)-1H-pyrrolo[2,3-b]pyridine;
5-(1-methyl-1H-pyrazol-4-yl)-3-[6-(piperidin-4-yloxy)pyrazin-2-yl]-1H-pyrrolo[2,3-b]pyridine;
3-[6-(cyclohexyloxy)pyrazin-2-yl]-5-(1-methyl-1H-pyrazol-4-yl)-1H-pyrrolo[2,3-b]pyridine;
N-methyl-6-[5-(1-methyl-1H-pyrazol-4-yl)-1H-pyrrolo[2,3-b]pyridin-3-yl]-N-piperidin-4-ylpyrazin-2-amine;
3-[6-(piperidin-4-yloxy)pyrazin-2-yl]-5-(1H-pyrazol-4-yl)-1H-pyrrolo[2,3-b]pyridine;
3-{6-[(3R)-piperdin-3-yloxy]pyrazin-2-yl}-5-(1H-pyrazol-4-yl)-1H-pyrrolo[2,3-b]pyridine;
3-{6-[(3S)-piperdin-3-yloxy]pyrazin-2-yl}-5-(1H-pyrazol-4-yl)-1H-pyrrolo[2,3-b]pyridine;
trans-3-{6-[(3-fluoropiperdin-4-yl)oxy]pyrazin-2-yl}-5-(1H-pyrazol-4-yl)-1H-pyrrolo[2,3-b]pyridine;
cis-3-{6-[(3-fluoropiperdin-4-yl)oxy]pyrazin-2-yl}-5-(1H-pyrazol-4-yl)-1H-pyrrolo[2,3-b]pyridine;
3-[6-(azetidine-3-yloxy)pyrazin-2-yl]-5-(1H-pyrazol-4-yl)-1H-pyrrolo[2,3-b]pyridine;
5-(1H-pyrazol-4-yl)-3-{6-[(3S)-pyrrolidin-3-yloxy]pyrazin-2-yl-1H-pyrrolo[2,3-b]pyridine;
(2S)-1-({6-[5-(1H-pyrazol-4-yl)-1H-pyrrolo[2,3-b]pyridin-3-yl]pyrazin-2-yl}oxy)propan-2-amine;
(2S)-2-({6-[5-(1H-pyrazol-4-yl)-1H-pyrrolo[2,3-b]pyridin-3-yl]pyrazin-2-yl}oxy)propan-1-amine;
5-(1H-pyrazol-4-yl)-3-{6-[(3R)-pyrrolidin-3-yloxy]pyrazin-2-yl-1H-pyrrolo[2,3-b]pyridine;

(2R)-1-({6-[5-(1H-pyrazol-4-yl)-1H-pyrrolo[2,3-b]pyridin-3-yl]pyrazin-2-yl}oxy)propan-2-amine;
(2R)-2-({6-[5-(1H-pyrazol-4-yl)-1H-pyrrolo[2,3-b]pyridin-3-yl]pyrazin-2-yl}oxy)propan-1-amine;
Trans-4-({6-[5-(1H-pyrazol-4-yl)-1H-pyrrolo[2,3-b]pyridin-3-yl]pyrazin-2-yl)}amino)cyclohexanol;
6-[5-(1H-pyrazol-4-yl)-1H-pyrrolo[2,3-b]pyridin-3-yl-N-(tetrahydro-2H-pyran-5-yl)pyrazin-2-amine;
1-{6-[5-(1H-pyrazol-4-yl)-1H-pyrrolo[2,3-b]pyridin-3-yl]pyrazin-2-yl}piperdin-4-ol;
2-({6-[5-(1H-pyrazol-4-yl)-1H-pyrrolo[2,3-b]pyridin-3-yl]pyrazin-2-yl}amino)ehthanol;
1-{6-[5-(1H-pyrazol-4-yl)-1H-pyrrolo[2,3-b]pyridin-3-yl]pyrazin-2-yl}azetidin-3-ol;
3-({6-[5-(1H-pyrazol-4-yl)-1H-pyrrolo[2,3-b]pyridin-3-yl]pyrazin-2-yl}amino)propan-1-ol;
4-({6-[5-(1H-pyrazol-4-yl)-1H-pyrrolo[2,3-b]pyridin-3-yl]pyrazin-2-yl}oxy)cyclohexanol;
5-(1-ethyl-1H-pyrazol-4-yl)-3-[6-(piperidin-4-yloxy)pyrazin-2-yl]-1H-pyrrolo[2,3-b]pyridine;
5-[1-(cyclopropylmethyl)-1H-pyrazol-4-yl]-3-[6-(piperidin-4-yloxy)pyrazin-2-yl]-1H-pyrrolo[2,3-b]pyridine;
2-(4-{3-[6-(piperidin-4-yloxy)pyrazin-2-yl]-1H-pyrrolo[2,3-b]pyridine-5-yl}-1H-pyrazol-1-yl)ethanol;
3-[6-(piperidin-4-yloxy)pyrazin-2-yl]-5-[1-(2,2,2-trifluoroethyl)-1H-pyrazol-4-yl]-1H-pyrrolo[2,3-b]pyridine;
3-[6-(piperidin-4-yloxy)pyrazin-2-yl]-1-(2,2,2-trifluoroethyl)-5-[1-(2,2,2-trifluoroethyl)-1H-pyrazol-4-yl]-1H-pyrrolo[2,3-b]pyridine;
5-(1H-pyrazol-4-yl)-3-(6-{[3-(trifluoromethyl)azetidin-3-yl]oxy}pyrazin-2-yl]-1H-pyrrolo[2,3-b]pyridine;
3,3,3-trifluoro-2-({6-[5-(1H-pyrazol-4-yl)-1H-pyrrolo[2,3-b]pyridin-3-yl]pyrazin-2-yl}oxy)propan-1-amine;
N-ethyl-N-piperidin-4-yl-6-[5-(1H-pyrazol-4-yl)-1H-pyrrolo[2,3-b]pyridin-3-yl]pyrazin-2-amine;
N-piperidin-4-yl-N-propyl-6-[5(1H-pyrazol-4-yl)-1H-pyrrolo[2,3-b]pyridin-3-yl]pyrazin-2-amine;
3-[5-methyl-6-(piperidin-4-yloxy)pyrazin-2-yl]-5-(1H-pyrazol-4-yl)-1H-pyrrolo[2,3-b]pyridine;
N-[2-({6-[5-(1H-pyrazol-4-yl)-1H-pyrrolo[2,3-b]pyridin-3-yl]pyrazin-2-yl}oxy)ethyl]cyclohexanamine;
and pharmaceutically acceptable salts, stereoisomers and tautomers thereof.

8. A pharmaceutical composition comprising a compound of claim 1, or a pharmaceutically acceptable salt or tautomer thereof in association with a pharmaceutically acceptable carrier.

* * * * *

```
                        SEQUENCE LISTING

<160> NUMBER OF SEQ ID NOS: 4

<210> SEQ ID NO 1
<211> LENGTH: 15
<212> TYPE: PRT
<213> ORGANISM: Artificial Sequence
<220> FEATURE:
<223> OTHER INFORMATION: Completely Synthetic Amino Acid Sequence
<221> NAME/KEY: AMIDATION
<222> LOCATION: (15)...(15)
<223> OTHER INFORMATION: C-terminus Amide

<400> SEQUENCE: 1

Glu Gln Glu Asp Glu Pro Glu Gly Asp Tyr Phe Glu Trp Leu Glu
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Completely Synthetic Amino Acid Sequence

<400> SEQUENCE: 2

Met Glu Tyr Met Pro Met Glu
1               5

<210> SEQ ID NO 3
<211> LENGTH: 6
<212> TYPE: PRT
<213> ORGANISM: Artificial Sequence
<220> FEATURE:
<223> OTHER INFORMATION: Completely Synthetic Amino Acid Sequence

<400> SEQUENCE: 3

Glu Tyr Met Pro Met Glu
1               5

<210> SEQ ID NO 4
<211> LENGTH: 28
<212> TYPE: PRT
<213> ORGANISM: Artificial Sequence
<220> FEATURE:
<223> OTHER INFORMATION: Completely Synthetic Amino Acid Sequence

<400> SEQUENCE: 4

Gly Gly Asp Gly Ala Thr Met Lys Thr Phe Cys Gly Gly Thr Pro Ser
1               5                   10                  15

Asp Gly Asp Pro Asp Gly Gly Glu Phe Thr Glu Phe
                20                  25
```